US010351861B2

(12) United States Patent
Olsen

(10) Patent No.: US 10,351,861 B2
(45) Date of Patent: Jul. 16, 2019

(54) SELECTION IN FUNGI

(71) Applicant: Novozymes A/S, Bagsvaerd (DK)

(72) Inventor: Carsten Lillelund Olsen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 137 days.

(21) Appl. No.: 15/296,433

(22) Filed: Oct. 18, 2016

(65) Prior Publication Data

US 2017/0029830 A1 Feb. 2, 2017

Related U.S. Application Data

(62) Division of application No. 14/403,355, filed as application No. PCT/EP2013/061052 on May 29, 2013, now Pat. No. 9,487,767.

(60) Provisional application No. 61/656,170, filed on Jun. 6, 2012.

(30) Foreign Application Priority Data

May 31, 2012 (EP) .................................... 12170260

(51) Int. Cl.

| | |
|---|---|
| ***C12N 15/80*** | (2006.01) |
| ***C12N 9/20*** | (2006.01) |
| ***C12N 15/90*** | (2006.01) |
| ***C12P 21/00*** | (2006.01) |
| ***C12N 9/06*** | (2006.01) |
| ***C12N 9/88*** | (2006.01) |
| ***C12N 15/67*** | (2006.01) |

(52) U.S. Cl.

CPC ........... *C12N 15/80* (2013.01); *C12N 9/0044* (2013.01); *C12N 9/20* (2013.01); *C12N 9/88* (2013.01); *C12N 15/67* (2013.01); *C12N 15/902* (2013.01); *C12P 21/00* (2013.01); *C12Y 107/01003* (2013.01); *C12Y 107/01004* (2013.01); *C12Y 402/01011* (2013.01)

(58) Field of Classification Search

None

See application file for complete search history.

(56) References Cited

U.S. PATENT DOCUMENTS

2004/0197854 A1 10/2004 Brody et al.

FOREIGN PATENT DOCUMENTS

| | | | |
|---|---|---|---|
| JP | 2007259787 | | 10/2007 |
| WO | 0190393 | A1 | 11/2001 |
| WO | 2012153142 | A2 | 11/2012 |

OTHER PUBLICATIONS

JP200759787 EBI access No. ANK67806.
Vitreschak et al, 2004, Trends Genet 20(1), 44-50.
Verhounig et al, 2010, PNAS 107(14), 6204-6209.
Tucker et al, 2005, Curr Opin Struct Biol 15(3), 342-8.
Shoji et al, 2005, FEMS Microbiol Lett, 244 (1), 41-46.
Serganov et al, 2006, Nature 441, 1167-1171.
Rogozin et al, 2012, Biol Direct 7 (1), 11.
Nudler et al, 2004, Trends Biochem Sci 29(1), 11-7.
Kubodera et al, 2003, FEBS Letters 555, 516-520.
Dixon et al, 2010, PNAS 107 (7), 2830-2835.
Borsuk et al, 2007, Biol Chem 388, 135-144.
Bauer et al, 2006, J Biotechnol124, 4-11.
Batey et al, 2006, Curr Opin Struc Biol 16(3), 299-306.
Yamauchi T., et al., Novel gene expression control polynucleotide having thiamine diphosphate TPP connecting structure formation region with stem loop formation region in TPP binding type riboswitch of eukaryote, for producing target protein, Patent Number, JP 200759787-A, Access No. ANK67806, Dec. 13, 2007.
Brys et al, 1996, RNA 2, 707-717.
Cellini et al, 1986, The EMBO Journal 5(5), 1023-1030.

*Primary Examiner* — Nancy A Treptow
(74) *Attorney, Agent, or Firm* — Robert Starnes

(57) ABSTRACT

The present invention relates to methods for constructing a recombinant fungal host cell comprising one or more copies of a polynucleotide construct integrated in its genome, said method comprising transforming a fungal host cell with an integrative polynucleotide construct comprising a first polynucleotide encoding a selectable marker, wherein the first polynucleotide, a 5' untranslated region thereof and/or a riboswitch operably linked therewith comprises a spliceosomal intron which has 5 nucleotides or less between its branch site and its acceptor site; and a second polynucleotide encoding a polypeptide of interest; as well as suitable polynucleotide constructs, resulting fungal host cells and methods of manufacture.

47 Claims, 6 Drawing Sheets

Specification includes a Sequence Listing.

Lane 1: Marker Lambda DNA digested with *Bst*EII.

Lane 2: Strain transformed with pCOIs1175.

Lane 3: The background strain.

SEQUENCE LISTING

<160> NUMBER OF SEQ ID NOS: 40

<210> SEQ ID NO 1
<211> LENGTH: 45
<212> TYPE: DNA
<213> ORGANISM: artificial sequence
<220> FEATURE:
<223> OTHER INFORMATION: Primer P722

<400> SEQUENCE: 1
atctcgagct cgcgaaagct tttcggtaaa tacactatca cacac 45

<210> SEQ ID NO 2
<211> LENGTH: 55
<212> TYPE: DNA
<213> ORGANISM: artificial sequence
<220> FEATURE:
<223> OTHER INFORMATION: Primer P723

<400> SEQUENCE: 2
gagctcctca tggtggatcc actagtgcat gccaagttgc aatgactatc atctg 55

<210> SEQ ID NO 3
<211> LENGTH: 36
<212> TYPE: DNA
<213> ORGANISM: artificial sequence
<220> FEATURE:
<223> OTHER INFORMATION: Primer P766

<400> SEQUENCE: 3
gtcattgcaa cttggccaac atgtcttcca agtcgc 36

<210> SEQ ID NO 4
<211> LENGTH: 38
<212> TYPE: DNA
<213> ORGANISM: artificial sequence
<220> FEATURE:
<223> OTHER INFORMATION: Primer P767

<400> SEQUENCE: 4
accatgatta cgccgcatta gtgatacccc actctaag 38

<210> SEQ ID NO 5
<211> LENGTH: 29
<212> TYPE: DNA
<213> ORGANISM: artificial sequence
<220> FEATURE:
<223> OTHER INFORMATION: Primer P769

<400> SEQUENCE: 5
ccgcggcaag ttgcaatgac tatcatctg 29

<210> SEQ ID NO 6
<211> LENGTH: 37
<212> TYPE: DNA
<213> ORGANISM: artificial sequence
<220> FEATURE:
<223> OTHER INFORMATION: Primer 771

<400> SEQUENCE: 6
aattcgaagg cctcccatca ccatcaccat cactaag 37

<210> SEQ ID NO 7
<211> LENGTH: 42
<212> TYPE: DNA
<213> ORGANISM: artificial sequence
<220> FEATURE:
<223> OTHER INFORMATION: Primer P503

<400> SEQUENCE: 7
acatgatcat ataaccaatt gccctcatcc ccatccttta ac 42

<210> SEQ ID NO 8
<211> LENGTH: 21
<212> TYPE: DNA
<213> ORGANISM: artificial sequence
<220> FEATURE:
<223> OTHER INFORMATION: Primer P782

<400> SEQUENCE: 8
ccttgatact ctgtgagcgc t 21

<210> SEQ ID NO 9
<211> LENGTH: 57
<212> TYPE: DNA
<213> ORGANISM: artificial sequence
<220> FEATURE:
<223> OTHER INFORMATION: Primer P783

<400> SEQUENCE: 9
gagctcctca tggggccgcg gcaatgacta tcatctgtta gccattccat caacagg 57

-continued

<210> SEQ ID NO 10
<211> LENGTH: 57
<212> TYPE: DNA
<213> ORGANISM: artificial sequence
<220> FEATURE:
<223> OTHER INFORMATION: Primer P784

<400> SEQUENCE: 10
gagctcctca tggggccgcg gcaatcaact atctcagtta gccattccat caacagg 57

<210> SEQ ID NO 11
<211> LENGTH: 57
<212> TYPE: DNA
<213> ORGANISM: artificial sequence
<220> FEATURE:
<223> OTHER INFORMATION: Primer P785

<400> SEQUENCE: 11
gagctcctca tggggccgcg gcaatcagac tattcagtta gccattccat caacagg 57

<210> SEQ ID NO 12
<211> LENGTH: 57
<212> TYPE: DNA
<213> ORGANISM: artificial sequence
<220> FEATURE:
<223> OTHER INFORMATION: Primer P786

<400> SEQUENCE: 12
gagctcctca tggggccgcg gcaatcatca ctatcagtta gccattccat caacagg 57

<210> SEQ ID NO 13
<211> LENGTH: 57
<212> TYPE: DNA
<213> ORGANISM: artificial sequence
<220> FEATURE:
<223> OTHER INFORMATION: Primer P787

<400> SEQUENCE: 13
gagctcctca tggggccgcg gcaatcatca actatcgtta gccattccat caacagg 57

<210> SEQ ID NO 14
<211> LENGTH: 57
<212> TYPE: DNA
<213> ORGANISM: artificial sequence
<220> FEATURE:
<223> OTHER INFORMATION: Primer P788

<400> SEQUENCE: 14
gagctcctca tggggccgcg gcaatcatca gactatgtta gccattccat caacagg 57

<210> SEQ ID NO 15
<211> LENGTH: 57
<212> TYPE: DNA
<213> ORGANISM: artificial sequence
<220> FEATURE:
<223> OTHER INFORMATION: Primer P789

<400> SEQUENCE: 15
gagctcctca tggggccgcg gcaatcatca tgactagtta gccattccat caacagg 57

<210> SEQ ID NO 16
<211> LENGTH: 57
<212> TYPE: DNA
<213> ORGANISM: artificial sequence
<220> FEATURE:
<223> OTHER INFORMATION: Primer P792

-continued

<400> SEQUENCE: 16
gagctcctca tggggccgcg gcaatgagga tcatctgtta gccattccat caacagg 57

<210> SEQ ID NO 17
<211> LENGTH: 51
<212> TYPE: DNA
<213> ORGANISM: artificial sequence
<220> FEATURE:
<223> OTHER INFORMATION: Primer P775

<400> SEQUENCE: 17
gatagtcatt gcaacttgcc gcggcaccat gtcttccaag tcgcaattga c 51

<210> SEQ ID NO 18
<211> LENGTH: 38
<212> TYPE: DNA
<213> ORGANISM: artificial sequence
<220> FEATURE:
<223> OTHER INFORMATION: Primer P767

<400> SEQUENCE: 18
accatgatta cgccgcatta gtgatacccc actctaag 38

<210> SEQ ID NO 19
<211> LENGTH: 20
<212> TYPE: DNA
<213> ORGANISM: artificial sequence
<220> FEATURE:
<223> OTHER INFORMATION: The 5'-end of the riboswitches in Example 5.

<400> SEQUENCE: 19
ccgctcccac acaattctct 20

<210> SEQ ID NO 20
<211> LENGTH: 13
<212> TYPE: DNA
<213> ORGANISM: artificial sequence
<220> FEATURE:
<223> OTHER INFORMATION: The 3'-end of the riboswitches in Example 5.

<400> SEQUENCE: 20
tcattgcaac ttg 13

<210> SEQ ID NO 21
<211> LENGTH: 8371
<212> TYPE: DNA
<213> ORGANISM: artificial sequence
<220> FEATURE:
<223> OTHER INFORMATION: Vector pCOls207

<400> SEQUENCE: 21
gccttcctgt ttttgctcac ccagaaacgc tggtgaaagt aaaagatgct gaagatcagt 60
tgggtgcacg agtgggttac atcgaactgg atctcaacag cggtaagatc cttgagagtt 120
ttcgccccga agaacgtttt ccaatgatga gcacttttaa agttctgcta tgtggcgcgg 180
tattatcccg tattgacgcc gggcaagagc aactcggtcg ccgcatacac tattctcaga 240
atgacttggt tgagtactca ccagtcacag aaaagcatct tacggatggc atgacagtaa 300
gagaattatg cagtgctgcc ataaccatga gtgataacac tgcggccaac ttacttctga 360
caacgatcgg aggaccgaag gagctaaccg cttttttgca caacatgggg gatcatgtaa 420
ctcgccttga tcgttgggaa ccggagctga atgaagccat accaaacgac gagcgtgaca 480
ccacgatgcc tgtagcaatg gcaacaacgt tgcgcaaact attaactggc gaactactta 540

-continued

```
ctctagcttc ccggcaacaa ttaatagact ggatggaggc ggataaagtt gcaggaccac    600
ttctgcgctc ggcccttccg gctggctggt ttattgctga taaatctgga gccggtgagc    660
gtgggtctcg cggtatcatt gcagcactgg ggccagatgg taagccctcc cgtatcgtag    720
ttatctacac gacggggagt caggcaacta tggatgaacg aaatagacag atcgctgaga    780
taggtgcctc actgattaag cattggtaac tgtcagacca agtttactca tatatacttt    840
agattgattt aaaacttcat ttttaattta aaaggatcta ggtgaagatc ctttttgata    900
atctcatgac caaaatccct taacgtgagt tttcgttcca ctgagcgtca gaccccgtag    960
aaaagatcaa aggatcttct tgagatcctt tttttctgcg cgtaatctgc tgcttgcaaa   1020
caaaaaaacc accgctacca gcggtggttt gtttgccgga tcaagagcta ccaactcttt   1080
ttccgaaggt aactggcttc agcagagcgc agataccaaa tactgtcctt ctagtgtagc   1140
cgtagttagg ccaccacttc aagaactctg tagcaccgcc tacatacctc gctctgctaa   1200
tcctgttacc agtggctgct gccagtggcg ataagtcgtg tcttaccggg ttggactcaa   1260
gacgatagtt accggataag gcgcagcggt cgggctgaac ggggggttcg tgcacacagc   1320
ccagcttgga gcgaacgacc tacaccgaac tgagatacct acagcgtgag ctatgagaaa   1380
gcgccacgct tcccgaaggg agaaaggcgg acaggtatcc ggtaagcggc agggtcggaa   1440
caggagagcg cacgagggag cttccagggg gaaacgcctg gtatctttat agtcctgtcg   1500
ggtttcgcca cctctgactt gagcgtcgat ttttgtgatg ctcgtcaggg gggcggagcc   1560
tatggaaaaa cgccagcaac gcggcctttt tacggttcct ggccttttgc tggccttttg   1620
ctcacatgtt ctttcctgcg ttatcccctg attctgtgga taaccgtatt accgcctttg   1680
agtgagctga taccgctcgc cgcagccgaa cgaccgagcg cagcgagtca gtgagcgagg   1740
aagcggaaga gcgcccaata cgcaaaccgc ctctccccgc gcgttggccg attcattaat   1800
gcagctggca cgacaggttt cccgactgga aagcgggcag tgagcgcaac gcaattaatg   1860
tgagttagct cactcattag gcaccccagg ctttacactt tatgcttccg gctcgtatgt   1920
tgtgtggaat tgtgagcgga taacaatttc acacaggaaa cagctatgac catgattacg   1980
ccaagctagc ttggcggtga tattgatggc acgatagaag cagcacattc tgtccctaga   2040
cttagagatt atcatgaaga tattctcgat caaatgcttt ttgcgctctt tctcagcaaa   2100
agacatgctg atgcagcgaa gctgctggaa agtattttcg gtacgatttt gacatttgct   2160
ccattgtcga ggatggatgg aacgagcggc gtgcgccacg aaagtgaggc tattgcctat   2220
cagctctttg ctacattccg gaaacaaaca tcccttttttg tgaattatct acgcaactta   2280
gatggcgtga acgcatcttc aaagtctttc ggcaggtccg gcacgacttt tgcatccaga   2340
gaagcgccta catgtgtatt cgaccacctc ctagcgcgct tggatatgag gaaatattac   2400
tgagagtcga aaacaagctc caccgcacca gctcttcttg gagttttata ttaaagaata   2460
ttcccagctc gttgtattat tctttttcta ccgtgctaat gtatcaagga ctttggtacc   2520
tattaacgtt attattcgtg tgctattccc aaacataacc ctgtatatgt ttcgaacgcc   2580
gttatgaccc atgtcttaca tactcattaa gtcattccct tggataatcc caatttagaa   2640
gaagtgaagg tctgattctt tccatccttc cgccaacagt atcctccgag ccgattcttc   2700
catggctggc ggaccacaaa tcaggaccat actctcatct tctggagccg cgtactcctt   2760
taggagctct tcggatatgc gtcctcggcg gccagtccat gagtccggcg ctttggatag   2820
ggtgtgtatt atattacacc ttctgctgtc ggttgccatg aagccgtcga gctcagcccg   2880
gcaaaggata tcttcctcct gtctgtttcc attgaggact gtacaagagg tgggatcttg   2940
```

-continued

```
ccggtcctga accacggcgc gcaagacctg gaagatcggt gtgataccgg ttcctccaca   3000
aatcatctta aacgaccgaa catggcgttc cttcccactt atgacaactc gtccatttcc   3060
aaggtattcg aatctgcctg tcggaccctt gcattccacc acggagccca atggcagcct   3120
atccagggcc atcgtcatct tgccgcctgc cgaggtggct gttgcaaagt atactttaac   3180
cagcaagtcc acggtccctt tctggctggt ttcagaaatt ggggtgtatg agcggatgat   3240
ggcttcgttg ttggatgatg tgtcgaggac tttgatcata agatgctggc cgactggtaa   3300
acccaatgtt tgatcttcgt gttccaattt gaaactaaat attcgtgtat cccaggatat   3360
gtctttcctt tctttcaatg ttgcctttgt ccaagaccgt gattggagga acactgggcg   3420
aatttcatcg gtggaggatg atgcatcatc cttgagtgct tttaaacctt ccgggtccat   3480
cgttccaata tggtactcag gcatcatcgc ctttgccgtc tcgctatcta tggataggtg   3540
tcaatagatg gtacaattgc agtgtgatat ttttgggact cacgaatagc aaggaattcc   3600
tcagagacat ccagaccagc agaggagata atactctgcg ctccgccagg gtggccttca   3660
agaaatgctt gaccatcata cacttctcca ttcacgatga accatggctt ctcatcgcag   3720
gaattctcct tgaattcttc aaaaccaatc actcggctta gcccgtcttt cttcatatta   3780
atgtcttgca cgggctccgg ctccgtcggc tcctctcctt cgtgtctttc tccccagtta   3840
ccattcgtca ggtcaccccc agccttttg acgcgttcca tccatcctgt aggcatacta   3900
gggtgggtag ggtgctcgaa tctcaagttc ccgttttcct tcgtaattgt aacccggaac   3960
cacgggttgt tcatcattcc gagaacggac cagtacatat cgcgaggctg cacgcccaat   4020
gcttcgtcca tggctcttac aaggatggca tcactgttct caagctctgg gatggtgatg   4080
cttagagacc aaaaacacca gcagaagcaa gtttcgcgcc agtacatatc tactttgcct   4140
ccaaaaagct cgccttcaaa atcacgatac ttgtcttcgg catattcgat ttccgccaat   4200
ctccaagcta taagtccgtt agctttgata agcattctca cacatcgagc gagcgagggt   4260
gcgtacattt gcctttgtct agggatattt ctaccctggt aaccctgcgg cccccaccgg   4320
cgtatgcata tcctctgaca gtatatgacg gccctgccga caggagattt aagacctcat   4380
tgttttgggg atatgcaacg gcggagttgg tgtttaggtc ataaatcgca taccgctcat   4440
cgtgccacca atttcggtta tttgatgcca tctcaggcga gaccattgtt ctgggttagg   4500
gagttagaca aatgatggaa atataaaata agtgcccttt agacatacgg taagacgcgg   4560
ttgtcattga tatggtacca gttgtcgctt ggtgcatcgg tcaagatcag cctcttcagc   4620
cacttaacac ttcgtcctcc tatttgaccg ggcacgacgg ccctcagcgg acgaccatga   4680
tctgggcgaa gagactcccc gttcatttta tgtgcaagca tgatcccccct gttggggtcc   4740
agggcccagt tcaatttaat agatgtgccg tagtgaccat tgggctgcgg cgaacttagc   4800
aattatcatc ataagataga ggtacagcat accagcttat ccgctccttc catacagacg   4860
tatttcgctt tacgcagggg tttcgcactg cggagaatat ccgccagcaa tgggccagtg   4920
aagagggcag tcgatagtcc cgccgatccc caggaaaaac ctttcgtttt acgtacaatg   4980
ttttgctctt tgcgtcgatt gccagcacat acgagggtga taggcgctgt tatttggtcg   5040
tactgctgca acacttgtcg gaagtttagt accaaaggct tctctaccag tctatacttt   5100
ggttaacgga tgtttggcag agaacctagc actatactaa cccttcgatg ctaatttccc   5160
agtgagggat atcttcatcc ttgatatgag ggactgggcc atgatttcga acatagaaga   5220
gctccggcga tgttaaaaac cctttcagag tgtgagaatg taacggctca aggggacaag   5280
catgacagcc ggtgcaagca acctgataag gataggagtg gagcagttat aactcatacc   5340
```

-continued

```
ttctttatac agatctcgag ctcgcgaaag ctttcgcgag ctcgagatct agatatcgat   5400
gaattcatgg tgttttgatc attttaaatt tttatatggc gggtggtggg caactcgctt   5460
gcgcgggcaa ctcgcttacc gattacgtta gggctgatat ttacgtaaaa atcgtcaagg   5520
gatgcaagac caaaccgtta aatttccgga gtcaacagca tccaagccca agtccttcac   5580
ggagaaaccc cagcgtccac atcacgagcg aaggaccacc tctaggcatc ggacgcacca   5640
tccaattaga agcagcaaag cgaaacagcc caagaaaaag gtcggcccgt cggccttttc   5700
tgcaacgctg atcacgggca gcgatccaac caacaccctc cagagtgact aggggcggaa   5760
atttatcggg attaatttcc actcaaccac aaatcacagt cgtccccggt aatttaacgg   5820
ctgcagacgg caatttaacg gcttctgcga atcgcttgga ttccccgccc ctggccgtag   5880
agcttaaagt atgtcccttg tcgatgcgat gtatcacaac atataaatac tggcaaggga   5940
tgccatgctt ggagtttcca actcaattta cctctatcca cacttctctt ccttcctcaa   6000
tcctctatat acacaactgg ggatccacca tgaggagctc ccttgtgctg ttctttgtct   6060
ctgcgtggac ggccttgggt atgtacacca ccccccttgcg tctgatctgt gacatatgta   6120
gctgactggt cagccagtcc tattcgtcga gaggtctcgc aggatctgtt taaccagttc   6180
aatctctttg cacagtattc tgcagccgca tactgcggaa aaaacaatga tgccccagct   6240
ggtacaaaca ttacgtgcac gggaaatgcc tgccccgagg tagagaaggc ggatgcaacg   6300
tttctctact cgtttgaaga ctctggagtg ggcgatgtca ccggcttcct tgctctcgac   6360
aacacgaaca aattgatcgt cctctctttc cgtggctctc gttccataga gaactggatc   6420
gggaatctta acttcgactt gaaagaaata aatgacattt gctccggctg caggggacat   6480
gacggcttca cttcgtcctg gaggtctgta gccgatacgt taaggcagaa ggtggaggat   6540
gctgtgaggg agcatcccga ctatcgcgtg gtgtttaccg gacatagctt gggtggtgca   6600
ttggcaactg ttgccggagc agacctgcgt ggaaatgggt atgatatcga cgtgttttca   6660
tatggcgccc cccgagtcgg aaacagggct tttgcagaat tcctgaccgt acagaccggc   6720
ggaacactct accgcattac ccacaccaat gatattgtcc ctagactccc gccgcgcgaa   6780
ttcggttaca gccattctag cccagagtac tggatcaaat ctggaaccct tgtccccgtc   6840
acccgaaacg atatcgtgaa gatagaaggc atcgatgcca ccggcggcaa taaccagcct   6900
aacattccgg atatccctgc gcacctatgg tacttcgggt taattgggac atgtctttag   6960
tgcgcggcgc ggctgggtcg actctagcga gctcgagatc tagagggtga ctgacacctg   7020
gcggtagaca atcaatccat ttcgctatag ttaaaggatg gggatgaggg caattggtta   7080
tatgatcatg tatgtagtgg gtgtgcataa tagtagtgaa atggaagcca agtcatgtga   7140
ttgtaatcga ccgacggaat tgaggatatc cggaaataca gacaccgtga aagccatggt   7200
ctttccttcg tgtagaagac cagacagaca gtccctgatt taccccttgca caaagcacta   7260
gaaaattagc attccatcct tctctgcttg ctctgctgat atcactgtca ttcaatgcat   7320
agccatgagc tcatcttaga tccaagcacg taattccata gccgaggtcc acagtggagc   7380
agcaacattc cccatcattg ctttccccag gggcctccca acgactaaat caagagtata   7440
tctctaccgt ccaatagatc gtcttcgctt caaaatcttt gacaattcca agagggtccc   7500
catccatcaa acccagttca ataatagccg agatgcatgg tggagtcaat taggcagtat   7560
tgctggaatg tcgggccagt tggccgggtg gtcattggcc gccagtacga ctgtgatgcc   7620
atctgccact aaatccgatc attgatccac cgcccacgag gcgcgtcttt gctttttgcg   7680
cggcgtccag gttcaactct ctcgctctag atatcgatga attcactggc cgtcgtttta   7740
```

-continued caacgtcgtg actgggaaaa ccctggcgtt acccaactta atcgccttgc agcacatccc 7800
cctttcgcca gctggcgtaa tagcgaagag gcccgcaccg atcgcccttc ccaacagttg 7860
cgcagcctga atggcgaatg gcgcctgatg cggtattttc tccttacgca tctgtgcggt 7920
atttcacacc gcatatggtg cactctcagt acaatctgct ctgatgccgc atagttaagc 7980
cagccccgac acccgccaac acccgctgac gcgccctgac gggcttgtct gctcccggca 8040
tccgcttaca gacaagctgt gaccgtctcc gggagctgca tgtgtcagag gttttcaccg 8100
tcatcaccga aacgcgcgag acgaaagggc ctcgtgatac gcctattttt ataggttaat 8160
gtcatgataa taatggtttc ttagacgtca ggtggcactt ttcggggaaa tgtgcgcgga 8220
acccctattt gtttattttt ctaaatacat tcaaatatgt atccgctcat gagacaataa 8280
ccctgataaa tgcttcaata atattgaaaa aggaagagta tgagtattca acatttccgt 8340
gtcgccctta ttcccttttt tgcggcattt t 8371

<210> SEQ ID NO 22
<211> LENGTH: 7466
<212> TYPE: DNA
<213> ORGANISM: artificial sequence
<220> FEATURE:
<223> OTHER INFORMATION: Plasmid pJaL1262

<400> SEQUENCE: 22
tgtataagct agcttccgtt aaattgccgt cgtcagccgt taaattaccg attaatcccg 60
ataaatttcc gagatctccg ttaaattgcc gttcgcagcc gttaaattac cggggacgac 120
cgataaattt ccgcgatgaa ttcatggtgt tttgatcatt ttaaattttt atatggcggg 180
tggtgggcaa ctcgcttgcg cggcaactc gcttaccgat tacgttaggg ctgatattta 240
cgtaaaaatc gtcaagggat gcaagaccaa accgttaaat ttccggagtc aacagcatcc 300
aagcccaagt ccttcacgga gaaaccccag cgtccacatc acgagcgaag gaccacctct 360
aggcatcgga cgcaccatcc aattagaagc agcaaagcga aacagcccaa gaaaaaggtc 420
ggcccgtcgg ccttttctgc aacgctgatc acgggcagcg atccaaccaa caccctccag 480
agtgactagg ggcggaaatt tatcgggatt aatttccact caaccacaaa tcacagtcgt 540
ccccggtaat ttaacggctg cagacggcaa tttaacggct tctgcgaatc gcttggattc 600
cccgcccctg gccgtagagc ttaaagtatg tcccttgtcg atgcgatgta tcacaacata 660
taaatactgg caagggatgc catgcttgga gtttccaact caatttacct ctatccacac 720
ttctcttcct tcctcaatcc tctatataca caactgggga tccaccatga ggagctccct 780
tgtgctgttc tttgtctctg cgtggacggc cttggccagt cctattcgtc gagaggtctc 840
gcaggatctg tttaaccagt tcaatctctt tgcacagtat tctgcagccg catactgcgg 900
aaaaaacaat gatgccccag ctggtacaaa cattacgtgc acgggaaatg cctgccccga 960
ggtagagaag gcggatgcaa cgtttctcta ctcgtttgaa gactctggag tgggcgatgt 1020
caccggcttc cttgctctcg acaacacgaa caaattgatc gtcctctctt tccgtggctc 1080
tcgttccata gagaactgga tcgggaatct taacttcgac ttgaaagaaa taaatgacat 1140
ttgctccggc tgcaggggac atgacggctt cacttcgtcc tggaggtctg tagccgatac 1200
gttaaggcag aaggtggagg atgctgtgag ggagcatccc gactatcgcg tggtgtttac 1260
cggacatagc ttgggtggtg cattggcaac tgttgccgga gcagacctgc gtggaaatgg 1320
gtatgatatc gacgtgtttt catatggcgc cccccgagtc ggaaacaggg cttttgcaga 1380
attcctgacc gtacagaccg gcggaacact ctaccgcatt acccacacca atgatattgt 1440

-continued

```
ccctagactc ccgccgcgcg aattcggtta cagccattct agcccagagt actggatcaa   1500
atctggaacc cttgtccccg tcacccgaaa cgatatcgtg aagatagaag gcatcgatgc   1560
caccggcggc aataaccagc ctaacattcc ggatatccct gcgcacctat ggtacttcgg   1620
gttaattggg acatgtcttt agtgcgcggc gcggctgggt cgactctagc gagctcgaga   1680
tctagagggt gactgacacc tggcggtaga caatcaatcc atttcgctat agttaaagga   1740
tggggatgag ggcaattggt tatatgatca tgtatgtagt gggtgtgcat aatagtagtg   1800
aaatggaagc caagtcatgt gattgtaatc gaccgacgga attgaggata tccggaaata   1860
cagacaccgt gaaagccatg gtctttcctt cgtgtagaag accagacaga cagtccctga   1920
tttacccttg cacaaagcac tagaaaatta gcattccatc cttctctgct tgctctgctg   1980
atatcactgt cattcaatgc atagccatga gctcatctta gatccaagca cgtaattcca   2040
tagccgaggt ccacagtgga gcagcaacat tccccatcat tgctttcccc aggggcctcc   2100
caacgactaa atcaagagta tatctctacc gtccaataga tcgtcttcgc ttcaaaatct   2160
ttgacaattc caagagggtc cccatccatc aaacccagtt caataatagc cgagatgcat   2220
ggtggagtca attaggcagt attgctggaa tgtcggggcc agttggccgg gtggtcattg   2280
gccgcctgtg atgccatctg ccactaaatc cgatcattga tccaccgccc acgaggcgcg   2340
tctttgcttt ttgcgcggcg tccaggttca actctctcct ctagactgga aacgcaaccc   2400
tgaagggatt cttcctttga gagatggaag cgtgtcatat ctcttcggtt ctacggcagg   2460
ttttttctg ctctttcgta gcatggcatg gtcacttcag cgcttattta cagttgctgg   2520
tattgatttc ttgtgcaaat tgctatctga cacttattag ctatggagtc accacatttc   2580
ccagcaactt ccccacttcc tctgcaatcg ccaacgtcct ctcttcactg agtctccgtc   2640
cgataacctg cactgcaacc ggtgccccat ggtacgcctc cggatcatac tcttcctgca   2700
cgagggcatc aagctcacta accgccttga aactctcatt cttcttatcg atgttcttat   2760
ccgcaaaggt aaccggaaca accacgctcg tgaaatccag caggttgatc acagaggcat   2820
acccatagta ccggaactgg tcatgccgta ccgcagcggt aggcgtaatc ggcgcgatga   2880
tggcgtccag ttccttcccg gccttttctt cagcctcccg ccatttctca aggtactcca   2940
tctggtaatt ccacttctgg agatgcgtgt cccagagctc gttcatgtta acagctttga   3000
tgttcgggtt cagtaggtct ttgatatttg gaatcgccgg ctcgccggat gcactgatat   3060
cgcgcattac gtcggcgctg ccgtcagccg cgtagatatg ggagatgaga tcgtggccga   3120
aatcgtgctt gtatggcgtc cacggggtca cggtgtgacc ggctttggcg agtgcggcga   3180
cggtggtttc cacgccgcgc aggataggag ggtgtggaag gacattgccg tcgaagttgt   3240
agtagccgat attgagcccg ccgttcttga tcttggaggc aataatgtcc gactcggact   3300
ggcgccaggg catggggatg accttggagt cgtatttcca tggctcctga ccgaggacgg   3360
atttggtgaa gaggcggagg tctaacatac ttcatcagtg actgccggtc tcgtatatag   3420
tataaaaagc aagaaaggag gacagtggag gcctggtata gagcaggaaa agaaggaaga   3480
ggcgaaggac tcaccctcaa cagagtgcgt aatcggcccg acaacgctgt gcaccgtctc   3540
ctgaccctcc atgctgttcg ccatctttgc atacggcagc cgcccatgac tcggccttag   3600
accgtacagg aagttgaacg cggccggcac tcgaatcgag ccaccgatat ccgttcctac   3660
accgatgacg ccaccacgaa tcccaacgat cgcaccctca ccaccagaac tgccgccgca   3720
cgaccagttc ttgttgcgtg ggttgacggt gcgcccgatg atgttgttga ctgtctcgca   3780
gaccatcagg gtctgcggga cagaggtctt gacgtagaag acggcaccgg ctttgcggag   3840
```

-continued

```
catggttgtc agaaccgagt ccccttcgtc gtacttgttt agccatgaga tgtagcccat   3900
tgatgtttcg tagccctggt ggcatatgtt agctgacaaa aagggacatc taacgactta   3960
ggggcaacgg tgtaccttga ctcgaagctg gtctttgaga gagatgggga ggccatggag   4020
tggaccaacg ggtctcttgt gctttgcgta gtattcatcg agttcccttg cctgcgcgag   4080
agcggcgtca gggaagaact cgtgggcgca gtttgtctgc acagaagcca gcgtcagctt   4140
gatagtccca taaggtggcg ttgttacatc tccctgagag gtagagggga ccctactaac   4200
tgctgggcga ttgctgcccg tttacagaat gctagcgtaa cttccaccga ggtcaactct   4260
ccggccgcca gcttggacac aagatctgca gcggaggcct ctgtgatctt cagttcggcc   4320
tctgaaagga tcaccgattt ctttgggaaa tcaataacgc tgtcttccgc aggcagcgtc   4380
tggactttcc attcatcagg gatggttttt gcgaggcggg cgcgcttatc agcggccagt   4440
tcttcccagg attgaggcat tctgtgttag cttatagtca ggatgttggc tcgacgagtg   4500
taaactggga gttggcatga gggttatgta ggcttcttta gccccgcatc cccctcattc   4560
tcctcattga tcccggggga gcggatggtg ttgataagag actaattata gggtttagct   4620
ggtgcctagc tggtgattgg ctggcttcgc cgaattttac gggccaagga aagctgcaga   4680
accgcggcac tggtaaacgg taattaagct atcagcccca tgctaacgag tttaaattac   4740
gtgtattgct gataaacacc aacagagctt tactgaaaga tgggagtcac ggtgtggctt   4800
ccccactgcg attattgcac aagcagcgag ggcgaacttg actgtcgtcg ctgagcagcc   4860
tgcagtcaaa catacatata tatcaaccgc gaagacgtct ggccttgtag aacacgacgc   4920
tccctagcaa cacctgccgt gtcagcctct acggttgtta cttgcattca ggatgctctc   4980
cagcgggcga gctattcaaa atattcaaag caggtatctc gtattgccag gattcagctg   5040
aagcaacagg tgccaaggaa atctgcgtcg gttctcatct gggcttgctc ggtcctggcg   5100
tagatctaga gtcgacctgc aggcatgcgg cgtaatcatg gtcatagctg tttcctgtgt   5160
gaaattgtta tccgctcaca attccacaca acatacgagc cggaagcata aagtgtaaag   5220
cctggggtgc ctaatgagtg agctaactca cattaattgc gttgcgctca ctgcccgctt   5280
tccagtcggg aaacctgtcg tgccagctgc attaatgaat cggccaacgc gcggggagag   5340
gcggtttgcg tattgggcgc tcttccgctt cctcgctcac tgactcgctg cgctcggtcg   5400
ttcggctgcg gcgagcggta tcagctcact caaaggcggt aatacggtta tccacagaat   5460
caggggataa cgcaggaaag aacatgtgag caaaaggcca gcaaaaggcc aggaaccgta   5520
aaaaggccgc gttgctggcg tttttccata ggctccgccc ccctgacgag catcacaaaa   5580
atcgacgctc aagtcagagg tggcgaaacc cgacaggact ataaagatac caggcgtttc   5640
cccctggaag ctccctcgtg cgctctcctg ttccgaccct gccgcttacc ggatacctgt   5700
ccgcctttct cccttcggga agcgtggcgc tttctcatag ctcacgctgt aggtatctca   5760
gttcggtgta ggtcgttcgc tccaagctgg gctgtgtgca cgaacccccc gttcagcccg   5820
accgctgcgc cttatccggt aactatcgtc ttgagtccaa cccggtaaga cacgacttat   5880
cgccactggc agcagccact ggtaacagga ttagcagagc gaggtatgta ggcggtgcta   5940
cagagttctt gaagtggtgg cctaactacg gctacactag aagaacagta tttggtatct   6000
gcgctctgct gaagccagtt accttcggaa aaagagttgg tagctcttga tccgacaaac   6060
aaaccaccgc tggtagcggt ggtttttttg tttgcaagca gcagattacg cgcagaaaaa   6120
aaggatctca agaagatcct ttgatctttt ctacggggtc tgacgctcag tggaacgaaa   6180
actcacgtta agggattttg gtcatgagat tatcaaaaag gatcttcacc tagatccttt   6240
```

-continued taaattaaaa atgaagtttt aaatcaatct aaagtatata tgagtaaact tggtctgaca 6300
gttaagcaag gattttctta acttcttcgg cgacagcatc accgacttcg gtggtactgt 6360
tggaaccacc taaatcacca gttctgatac ctgcatccaa aaccttttta actgcatctt 6420
caatggcctt accttcttca ggcaagttca atgacaattt caacatcatt gcagcagaca 6480
agatagtggc gatagggttg accttattct ttggcaaatc tggagcagaa ccgtggcatg 6540
gttcgtacaa accaaatgcg gtgttcttgt ctggcaaaga ggccaaggac gcagatggca 6600
acaaacccaa ggaacctggg ataacggagg cttcatcgga gatgatatca ccaaacatgt 6660
tgctggtgat tataatacca tttaggtggg ttgggttctt aactaggatc atggcggcag 6720
aatcaatcaa ttgatgttga accttcaatg tagggaattc gttcttgatg gtttcctcca 6780
cagtttttct ccataatctt gaagaggcca aaacattagc tttatccaag gaccaaatag 6840
gcaatggtgg ctcatgttgt agggccatga aagcggccat tcttgtgatt ctttgcactt 6900
ctggaacggt gtattgttca ctatcccaag cgacaccatc accatcgtct tcctttctct 6960
taccaaagta aatacctccc actaattctc tgacaacaac gaagtcagta cctttagcaa 7020
attgtggctt gattggagat aagtctaaaa gagagtcgga tgcaaagtta catggtctta 7080
agttggcgta caattgaagt tctttacgga tttttagtaa accttgttca ggtctaacac 7140
tgccggtacc ccatttagga ccacccacag cacctaacaa aacggcatca gccttcttgg 7200
aggcttccag cgcctcatct ggaagtggaa cacctgtagc atcgatagca gcaccaccaa 7260
ttaaatgatt ttcgaaatcg aacttgacat tggaacgaac atcagaaata gctttaagaa 7320
ccttaatggc ttcggctgtg atttcttgac caacgtggtc acctggcaaa acgacgatct 7380
tcttaggggc agacatactc ttccttttc aatattattg aagcatttat cagggttatt 7440
gtctcatgag cggatacata tttgaa 7466

<210> SEQ ID NO 23
<211> LENGTH: 8487
<212> TYPE: DNA
<213> ORGANISM: artificial sequence
<220> FEATURE:
<223> OTHER INFORMATION: Plasmid pCOls1118

<400> SEQUENCE: 23
ctagcttggc ggtgatattg atggcacgat agaagcagca cattctgtcc ctagacttag 60
agattatcat gaagatattc tcgatcaaat gctttttgcg ctctttctca gcaaaagaca 120
tgctgatgca gcgaagctgc tggaaagtat tttcggtacg attttgacat ttgctccatt 180
gtcgaggatg gatggaacga gcggcgtgcg ccacgaaagt gaggctattg cctatcagct 240
ctttgctaca ttccggaaac aaacatccct ttttgtgaat tatctacgca acttagatgg 300
cgtgaacgca tcttcaaagt ctttcggcag gtccggcacg acttttgcat ccagagaagc 360
gcctacatgt gtattcgacc acctcctagc gcgcttggat atgaggaaat attactgaga 420
gtcgaaaaca agctccaccg caccagctct tcttggagtt ttatattaaa gaatattccc 480
agctcgttgt attattcttt ttctaccgtg ctaatgtatc aaggactttg gtacctatta 540
acgttattat tcgtgtgcta ttcccaaaca taaccctgta tatgtttcga acgccgttat 600
gacccatgtc ttacatactc attaagtcat tcccttggat aatcccaatt tagaagaagt 660
gaaggtctga ttctttccat ccttccgcca acagtatcct ccgagccgat tcttccatgg 720
ctggcggacc acaaatcagg accatactct catcttctgg agccgcgtac tcctttagga 780
gctcttcgga tatgcgtcct cggcggccag tccatgagtc cggcgctttg gatagggtgt 840

-continued

```
gtattatatt acaccttctg ctgtcggttg ccatgaagcc gtcgagctca gcccggcaaa    900
ggatatcttc ctcctgtctg tttccattga ggactgtaca agaggtggga tcttgccggt    960
cctgaaccac ggcgcgcaag acctggaaga tcggtgtgat accggttcct ccacaaatca   1020
tcttaaacga ccgaacatgg cgttccttcc cacttatgac aactcgtcca tttccaaggt   1080
attcgaatct gcctgtcgga cccttgcatt ccaccacgga gcccaatggc agcctatcca   1140
gggccatcgt catcttgccg cctgccgagg tggctgttgc aaagtatact ttaaccagca   1200
agtccacggt ccctttctgg ctggtttcag aaattggggt gtatgagcgg atgatggctt   1260
cgttgttgga tgatgtgtcg aggactttga tcataagatg ctggccgact ggtaaaccca   1320
atgtttgatc ttcgtgttcc aatttgaaac taaatattcg tgtatcccag gatatgtctt   1380
tcctttcttt caatgttgcc tttgtccaag accgtgattg gaggaacact gggcgaattt   1440
catcggtgga ggatgatgca tcatccttga gtgcttttaa accttccggg tccatcgttc   1500
caatatggta ctcaggcatc atcgcctttg ccgtctcgct atctatggat aggtgtcaat   1560
agatggtaca attgcagtgt gatatttttg ggactcacga atagcaagga attcctcaga   1620
gacatccaga ccagcagagg agataatact ctgcgctccg ccagggtggc cttcaagaaa   1680
tgcttgacca tcatacactt ctccattcac gatgaaccat ggcttctcat cgcaggaatt   1740
ctccttgaat tcttcaaaac caatcactcg gcttagcccg tctttcttca tattaatgtc   1800
ttgcacgggc tccggctccg tcggctcctc tccttcgtgt ctttctcccc agttaccatt   1860
cgtcaggtca cccccagcct ttttgacgcg ttccatccat cctgtaggca tactagggtg   1920
ggtagggtgc tcgaatctca agttcccgtt ttccttcgta attgtaaccc ggaaccacgg   1980
gttgttcatc attccgagaa cggaccagta catatcgcga ggctgcacgc ccaatgcttc   2040
gtccatggct cttacaagga tggcatcact gttctcaagc tctgggatgg tgatgcttag   2100
agaccaaaaa caccagcaga agcaagtttc gcgccagtac atatctactt tgcctccaaa   2160
aagctcgcct tcaaaatcac gatacttgtc ttcggcatat tcgatttccg ccaatctcca   2220
agctataagt ccgttagctt tgataagcat tctcacacat cgagcgagcg agggtgcgta   2280
catttgcctt tgtctaggga tatttctacc ctggtaaccc tgcggccccc accggcgtat   2340
gcatatcctc tgacagtata tgacggccct gccgacagga gatttaagac ctcattgttt   2400
tggggatatg caacggcgga gttggtgttt aggtcataaa tcgcataccg ctcatcgtgc   2460
caccaatttc ggttatttga tgccatctca ggcgagacca ttgttctggg ttagggagtt   2520
agacaaatga tggaaatata aaataagtgc cctttagaca tacggtaaga cgcggttgtc   2580
attgatatgg taccagttgt cgcttggtgc atcggtcaag atcagcctct tcagccactt   2640
aacacttcgt cctcctattt gaccgggcac gacggccctc agcggacgac catgatctgg   2700
gcgaagagac tccccgttca ttttatgtgc aagcatgatc cccctgttgg ggtccagggc   2760
ccagttcaat ttaatagatg tgccgtagtg accattgggc tgcggcgaac ttagcaatta   2820
tcatcataag atagaggtac agcataccag cttatccgct ccttccatac agacgtattt   2880
cgctttacgc aggggtttcg cactgcggag aatatccgcc agcaatgggc cagtgaagag   2940
ggcagtcgat agtcccgccg atccccagga aaaacctttc gttttacgta caatgttttg   3000
ctctttgcgt cgattgccag cacatacgag ggtgataggc gctgttattt ggtcgtactg   3060
ctgcaacact tgtcggaagt ttagtaccaa aggcttctct accagtctat actttggtta   3120
acggatgttt ggcagagaac ctagcactat actaaccctt cgatgctaat ttcccagtga   3180
gggatatctt catccttgat atgagggact gggccatgat ttcgaacata gaagagctcc   3240
```

-continued

```
ggcgatgtta aaaacccttt cagagtgtga gaatgtaacg gctcaagggg acaagcatga   3300
cagccggtgc aagcaacctg ataaggatag gagtggagca gttataactc ataccttctt   3360
tatacagatc tcgagctcgc gaaagcttaa ttctcgatga tcgggaagca agacttgagc   3420
gccgagagaa gcagttagac tatcgaacac gaatgctgga tgtgttagat gagagattgg   3480
atgatgcctt gcgccgacgc atgtccctga gagacgctgg tccgtattac tctcgacagt   3540
attatgaaaa ttattgattt gagttctctt ttccttgcat ttttcggttt ttatgattcc   3600
ccttctgttt gaatgttcct cttatcctcg ggccgctttt tctgttagtt tctattattc   3660
ttttcgggtg tgagtggggg atagacacta ataacgtcat tcaccgggga ccgttttgta   3720
taccagtgtt gtcgcgacct gttgcgttta gtgtatgttc cacgtatgta ctttctctaa   3780
aaaaaagtcg aatgagtcat gagaatgaga tatgatatgc accttaccgc actataactg   3840
ggatcattgt atagtatgga tctgtagagg acaggatgtt cagggccaag tcagcagttg   3900
acagcgcatt gcatccggtg acgagaactt atcgataagc cccaccagtg ccggcctcag   3960
gcagtccaac ccccgccata gagtgggatt gatttggttc gtttttcttc cgtcttccac   4020
cttttatgtc atcgctcttc cctgtcgtct gatcttcttc tactctttct tccatactga   4080
acttgacaat caccctgtct tttctcaatc aaactcgtcg tatcttactt ccacataaac   4140
acacattgga tccaccatga ggagctccct tgtgctgttc tttgtctctg cgtggacggc   4200
cttgggtaag aatcacttat aactagtaga ttaagccaag agtattggaa ctgatgataa   4260
acagccagtc ctattcgtcg agaggtctcg caggatctgt ttaaccagtt caatctcttt   4320
gcacagtatt ctgcagccgc atactgcgga aaaaacaatg atgccccagc tggtacaaac   4380
attacgtgca cgggaaatgc ctgccccgag gtagagaagg cggatgcaac gtttctctac   4440
tcgtttgaag actctggagt gggcgatgtc accggcttcc ttgctctcga caacacgaac   4500
aaattgatcg tcctctcttt ccgtggctct cgttccatag agaactggat cgggaatctt   4560
aacttcgact tgaaagaaat aaatgacatt tgctccggct gcaggggaca tgacggcttc   4620
acttcgtcct ggaggtctgt agccgatacg ttaaggcaga aggtggagga tgctgtgagg   4680
gagcatcccg actatcgcgt ggtgtttacc ggacatagct tgggtggtgc attggcaact   4740
gttgccggag cagacctgcg tggaaatggg tatgatatcg acgtgttttc atatggcgcc   4800
ccccgagtcg gaaacagggc ttttgcagaa ttcctgaccg tacagaccgg cggaacactc   4860
taccgcatta cccacaccaa tgatattgtc cctagactcc cgccgcgcga attcggttac   4920
agccattcta gcccagagta ctggatcaaa tctggaaccc ttgtccccgt cacccgaaac   4980
gatatcgtga agatagaagg catcgatgcc accggcggca ataaccagcc taacattccg   5040
gatatccctg cgcacctatg gtacttcggg ttaattggga catgtcttta gtgcgcggcg   5100
cggctgggtc gactctagcg agctcgagat ctagagggtg actgacacct ggcggtagac   5160
aatcaatcca tttcgctata gttaaaggat ggggatgagg gcaattggtt atatgatcat   5220
gtatgtagtg ggtgtgcata atagtagtga aatggaagcc aagtcatgtg attgtaatcg   5280
accgacggaa ttgaggatat ccggaaatac agacaccgtg aaagccatgg tctttccttc   5340
gtgtagaaga ccagacagac agtccctgat ttacccttgc acaaagcact agaaaattag   5400
cattccatcc ttctctgctt gctctgctga tatcactgtc attcaatgca tagccatgag   5460
ctcatcttag atccaagcac gtaattccat agccgaggtc cacagtggag cagcaacatt   5520
ccccatcatt gctttcccca ggggcctccc aacgactaaa tcaagagtat atctctaccg   5580
tccaatagat cgtcttcgct tcaaaatctt tgacaattcc aagagggtcc ccatccatca   5640
```

```
aacccagttc aataatagcc gagatgcatg gtggagtcaa ttaggcagta ttgctggaat   5700
gtcgggccag ttggccgggt ggtcattggc cgccagtacg actgtgatgc catctgccac   5760
taaatccgat cattgatcca ccgcccacga ggcgcgtctt tgctttttgc gcggcgtcca   5820
ggttcaactc tctcgctcta gatatcgatg aattcactgg ccgtcgtttt acaacgtcgt   5880
gactgggaaa accctggcgt tacccaactt aatcgccttg cagcacatcc ccctttcgcc   5940
agctggcgta atagcgaaga ggcccgcacc gatcgccctt cccaacagtt gcgcagcctg   6000
aatggcgaat ggcgcctgat gcggtatttt ctccttacgc atctgtgcgg tatttcacac   6060
cgcatatggt gcactctcag tacaatctgc tctgatgccg catagttaag ccagccccga   6120
cacccgccaa cacccgctga cgcgccctga cgggcttgtc tgctcccggc atccgcttac   6180
agacaagctg tgaccgtctc cgggagctgc atgtgtcaga ggttttcacc gtcatcaccg   6240
aaacgcgcga gacgaaaggg cctcgtgata cgcctatttt tataggttaa tgtcatgata   6300
ataatggttt cttagacgtc aggtggcact tttcggggaa atgtgcgcgg aacccctatt   6360
tgtttatttt tctaaataca ttcaaatatg tatccgctca tgagacaata accctgataa   6420
atgcttcaat aatattgaaa aaggaagagt atgagtattc aacatttccg tgtcgccctt   6480
attccctttt ttgcggcatt ttgccttcct gtttttgctc acccagaaac gctggtgaaa   6540
gtaaaagatg ctgaagatca gttgggtgca cgagtgggtt acatcgaact ggatctcaac   6600
agcggtaaga tccttgagag ttttcgcccc gaagaacgtt ttccaatgat gagcactttt   6660
aaagttctgc tatgtggcgc ggtattatcc cgtattgacg ccgggcaaga gcaactcggt   6720
cgccgcatac actattctca gaatgacttg gttgagtact caccagtcac agaaaagcat   6780
cttacggatg gcatgacagt aagagaatta tgcagtgctg ccataaccat gagtgataac   6840
actgcggcca acttacttct gacaacgatc ggaggaccga aggagctaac cgcttttttg   6900
cacaacatgg gggatcatgt aactcgcctt gatcgttggg aaccggagct gaatgaagcc   6960
ataccaaacg acgagcgtga caccacgatg cctgtagcaa tggcaacaac gttgcgcaaa   7020
ctattaactg gcgaactact tactctagct tcccggcaac aattaataga ctggatggag   7080
gcggataaag ttgcaggacc acttctgcgc tcggcccttc cggctggctg gtttattgct   7140
gataaatctg gagccggtga gcgtgggtct cgcggtatca ttgcagcact ggggccagat   7200
ggtaagccct cccgtatcgt agttatctac acgacgggga gtcaggcaac tatggatgaa   7260
cgaaatagac agatcgctga gataggtgcc tcactgatta agcattggta actgtcagac   7320
caagtttact catatatact ttagattgat ttaaaacttc atttttaatt taaaaggatc   7380
taggtgaaga tcctttttga taatctcatg accaaaatcc cttaacgtga gttttcgttc   7440
cactgagcgt cagaccccgt agaaaagatc aaaggatctt cttgagatcc tttttttctg   7500
cgcgtaatct gctgcttgca aacaaaaaaa ccaccgctac cagcggtggt ttgtttgccg   7560
gatcaagagc taccaactct ttttccgaag gtaactggct tcagcagagc gcagatacca   7620
aatactgtcc ttctagtgta gccgtagtta ggccaccact tcaagaactc tgtagcaccg   7680
cctacatacc tcgctctgct aatcctgtta ccagtggctg ctgccagtgg cgataagtcg   7740
tgtcttaccg ggttggactc aagacgatag ttaccggata aggcgcagcg gtcgggctga   7800
acggggggtt cgtgcacaca gcccagcttg gagcgaacga cctacaccga actgagatac   7860
ctacagcgtg agctatgaga aagcgccacg cttcccgaag ggagaaaggc ggacaggtat   7920
ccggtaagcg gcagggtcgg aacaggagag cgcacgaggg agcttccagg gggaaacgcc   7980
tggtatcttt atagtcctgt cgggtttcgc cacctctgac ttgagcgtcg atttttgtga   8040
```

-continued tgctcgtcag gggggcggag cctatggaaa aacgccagca acgcggcctt tttacggttc 8100
ctggcctttt gctggccttt tgctcacatg ttctttcctg cgttatcccc tgattctgtg 8160
gataaccgta ttaccgcctt tgagtgagct gataccgctc gccgcagccg aacgaccgag 8220
cgcagcgagt cagtgagcga ggaagcggaa gagcgcccaa tacgcaaacc gcctctcccc 8280
gcgcgttggc cgattcatta atgcagctgg cacgacaggt ttcccgactg gaaagcgggc 8340
agtgagcgca acgcaattaa tgtgagttag ctcactcatt aggcacccca ggctttacac 8400
tttatgcttc cggctcgtat gttgtgtgga attgtgagcg gataacaatt tcacacagga 8460
aacagctatg accatgatta cgccaag 8487

<210> SEQ ID NO 24
<211> LENGTH: 25
<212> TYPE: DNA
<213> ORGANISM: artificial sequence
<220> FEATURE:
<223> OTHER INFORMATION: Sequence from Example 7 with STOP codons in all 3 reading frames.

<400> SEQUENCE: 24
tgtacattga ttaattgaca ccatg 25

<210> SEQ ID NO 25
<211> LENGTH: 39
<212> TYPE: DNA
<213> ORGANISM: artificial sequence
<220> FEATURE:
<223> OTHER INFORMATION: Intron (6) from Example 7.

<400> SEQUENCE: 25
ctaacagttg atagtgtaca ttgattaatt gacaccatg 39

<210> SEQ ID NO 26
<211> LENGTH: 38
<212> TYPE: DNA
<213> ORGANISM: artificial sequence
<220> FEATURE:
<223> OTHER INFORMATION: Intron (5) from Example 7.

<400> SEQUENCE: 26
ctaacgttga tagtgtacat tgattaattg acaccatg 38

<210> SEQ ID NO 27
<211> LENGTH: 37
<212> TYPE: DNA
<213> ORGANISM: artificial sequence
<220> FEATURE:
<223> OTHER INFORMATION: Intron (4) from Example 7.

<400> SEQUENCE: 27
ctaacttgat agtgtacatt gattaattga caccatg 37

<210> SEQ ID NO 28
<211> LENGTH: 36
<212> TYPE: DNA
<213> ORGANISM: artificial sequence
<220> FEATURE:
<223> OTHER INFORMATION: Intron (3) from Example 7.

<400> SEQUENCE: 28
ctaactgata gtgtacattg attaattgac accatg 36

-continued

<210> SEQ ID NO 29
<211> LENGTH: 35
<212> TYPE: DNA
<213> ORGANISM: artificial sequence
<220> FEATURE:
<223> OTHER INFORMATION: Intron (2) from Example 7.

<400> SEQUENCE: 29
ctaacgatag tgtacattga ttaattgaca ccatg 35

<210> SEQ ID NO 30
<211> LENGTH: 34
<212> TYPE: DNA
<213> ORGANISM: artificial sequence
<220> FEATURE:
<223> OTHER INFORMATION: Intron (1) from Example 7.

<400> SEQUENCE: 30
ctaacatagt gtacattgat taattgacac catg 34

<210> SEQ ID NO 31
<211> LENGTH: 33
<212> TYPE: DNA
<213> ORGANISM: artificial sequence
<220> FEATURE:
<223> OTHER INFORMATION: Intron (0) from Example 7.

<400> SEQUENCE: 31
ctaactagtg tacattgatt aattgacacc atg 33

<210> SEQ ID NO 32
<211> LENGTH: 32
<212> TYPE: DNA
<213> ORGANISM: artificial sequence
<220> FEATURE:
<223> OTHER INFORMATION: Intron (-1) from Example 7.

<400> SEQUENCE: 32
ctaacagtgt acattgatta attgacacca tg 32

<210> SEQ ID NO 33
<211> LENGTH: 20
<212> TYPE: DNA
<213> ORGANISM: artificial sequence
<220> FEATURE:
<223> OTHER INFORMATION: Intron(6) from Example 1.

<400> SEQUENCE: 33
ctaacagatg atagtcattg 20

<210> SEQ ID NO 34
<211> LENGTH: 20
<212> TYPE: DNA
<213> ORGANISM: artificial sequence
<220> FEATURE:
<223> OTHER INFORMATION: Intron(5) from Example 1.

<400> SEQUENCE: 34
ctaactgaga tagttgattg 20

<210> SEQ ID NO 35
<211> LENGTH: 20
<212> TYPE: DNA
<213> ORGANISM: artificial sequence
<220> FEATURE:
<223> OTHER INFORMATION: Intron(4) from Example 1.

-continued

```
<400> SEQUENCE: 35

ctaactgaat agtctgattg                                                   20


<210> SEQ ID NO 36
<211> LENGTH: 20
<212> TYPE: DNA
<213> ORGANISM: artificial sequence
<220> FEATURE:
<223> OTHER INFORMATION: Intron(3) from Example 1.

<400> SEQUENCE: 36

ctaactgata gtgatgattg                                                   20


<210> SEQ ID NO 37
<211> LENGTH: 20
<212> TYPE: DNA
<213> ORGANISM: artificial sequence
<220> FEATURE:
<223> OTHER INFORMATION: Intron(2) from Example 1.

<400> SEQUENCE: 37

ctaacgatag ttgatgattg                                                   20


<210> SEQ ID NO 38
<211> LENGTH: 20
<212> TYPE: DNA
<213> ORGANISM: artificial sequence
<220> FEATURE:
<223> OTHER INFORMATION: Intron(1) from Example 1.

<400> SEQUENCE: 38

ctaacatagt ctgatgattg                                                   20


<210> SEQ ID NO 39
<211> LENGTH: 20
<212> TYPE: DNA
<213> ORGANISM: artificial sequence
<220> FEATURE:
<223> OTHER INFORMATION: Intron(0) from Example 1.

<400> SEQUENCE: 39

ctaactagtc atgatgattg                                                   20


<210> SEQ ID NO 40
<211> LENGTH: 20
<212> TYPE: DNA
<213> ORGANISM: artificial sequence
<220> FEATURE:
<223> OTHER INFORMATION: Intron(-1) from Example 1.

<400> SEQUENCE: 40

ctaacagatg atcctcattg                                                   20
```

SELECTION IN FUNGI

CROSS-REFERENCE TO RELATED APPLICATIONS

This application is a divisional application of U.S. patent application Ser. No. 14/403,355 filed May 29, 2013, now U.S. Pat. No. 9,487,767, which is a 35 U.S.C. § 371 national application of PCT/EP2013/061052 filed on May 29, 2013, which claims priority or the benefit under 35 U.S.C. § 119 of European Application No. 12170260.9 filed on May 31, 2012 and U.S. Provisional Application No. 61/656,170 filed on Jun. 6, 2012, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to methods for constructing a recombinant fungal host cell comprising one or more copies of a polynucleotide construct integrated in its genome, said method comprising transforming a fungal host cell with an integrative polynucleotide construct comprising a first polynucleotide encoding a selectable marker, wherein the first polynucleotide, a 5' untranslated region thereof and/or a riboswitch operably linked therewith comprises a spliceosomal intron which has 5 nucleotides or less between its branch site and its acceptor site; and a second polynucleotide encoding a polypeptide of interest; as well as suitable polynucleotide constructs, resulting fungal host cells and methods of manufacture.

BACKGROUND OF THE INVENTION

It is desirable for the biotech industry to provide microbial strains devoid of antibiotic resistance markers comprising several chromosomally integrated copies of a gene of interest, for the industrial high yield production of polypeptides. Antibiotic marker genes have traditionally been used as a means to select for strains carrying multiple copies of both the marker gene and an accompanying expression cassette coding for a polypeptide of industrial interest. Amplification of the expression cassette by increasing the copy number in a microbiological production strain was desirable because there is very often a direct correlation between the number of copies and the final product yields. Amplification methods using antibiotic selection markers have been used extensively in many host strains over the past 20 years and have proven to be a very efficient way to develop high yielding production strains in a relatively short time, irrespective of the expression level of the individual expression cassettes.

It has previously been shown in *Bacillus* that a galactose epimerase-encoding gene expressed from a crippled low-level promoter could be used as a selection marker for site-specific genomic integration of tandemly amplified copies of a product-gene (WO 2001/90393; Novozymes A/S). However, no similar systems have been described for fungal host cells.

A riboswitch is part of an mRNA molecule that can bind directly to a small target molecule without a protein being involved. Binding of the small target molecule will affect the translation of the mRNA [Nudler E, Mironov A S (2004). "The riboswitch control of bacterial metabolism". Trends Biochem Sci 29 (1): 11-7; Vitreschak A G, Rodionov D A, Mironov A A, Gelfand M S (2004). "Riboswitches: the oldest mechanism for the regulation of gene expression?". Trends Genet 20 (1): 44-50; Tucker B J, Breaker R R (2005). "Riboswitches as versatile gene control elements". Curr Opin Struct Biol 15 (3): 342-8; Batey R T (2006). "Structures of regulatory elements in mRNAs". Curr Opin Struct Biol 16 (3): 299-306].

In the filamentous fungal cell *Aspergillus oryzae* expression of the thiA and nmtA genes are regulated by riboswitches that bind thiamine pyrophosphate (TPP) and controls alternative splicing to conditionally produce an upstream Open Reading Frame (ORF), thereby affecting the expression of the downstream gene(s). The thiA riboswitch of *A. oryzae* contains a nuclear pre-mRNA intron, a spliceosomal intron, which is involved in facilitating the alternative splicing.

Another filamentous fungal riboswitch has been found in *Aspergillus nidulans*, where the agaA gene is regulated by mRNA arginine-binding, thereby facilitating alternative splicing [Borsuk, P. et al. (2007). "L-Arginine influences the structure and function of arginase mRNA in *Aspergillus nidulans*". Biol Chem. 388: 135-144].

In order to comply with the current demand for recombinant fungal production host strains devoid of antibiotic markers, we have looked for possible alternatives to produce multi-copy host strains.

SUMMARY OF THE INVENTION

The inventors found that by varying the number of nucleotides between the branch site and the acceptor site in a spliceosomal intron located in the 5' untranslated region of a downstream gene, the splicing efficiency could be adjusted to provide a surprisingly large expression range for the downstream gene. The number of nucleotides in the wild-type intron was 6 and the inventors successively removed each nucleotide until the branch site and the acceptor site actually overlapped with one nucleotide. This library of intron variant provided an astonishing range of expression levels of a downstream gene, from normal expression to an extremely low level of expression, as the examples below demonstrate. The inventors expect this to be the case also for spliceosomal introns located within the coding sequence of a gene.

Low expression levels are particularly interesting in the context of selectable markers comprised in polynucleotide constructs to be integrated into the genome of fungal host cells, because they make it possible to select for transformed cells, wherein the polynucleotide constructs have been integrated into the genome in multiple tandemly amplified copies. This selection is made possible because those cells having many copies of a selectable marker expressed at sufficiently low levels will have a growth advantage over cells with fewer copies, when cultivated under selective pressure. The expression cassette in the integrative construct will be amplified along with the selection marker, thereby ensuring a higher product yield.

Further, the particular spliceosomal intron investigated by the inventors herein was located within a so-called riboswitch, the thiA riboswitch of *Aspergillus oryzae*, where it is normally involved in the alternative splicing of the pre-mRNA of that gene, thereby regulating its expression level depending on whether or not there is enough thiamine (or rather, thiamine-pyrophosphate, TPP) for the cell's needs. Notwithstanding the surprisingly wide range of expression levels displayed by the intron variants created herein, the inventors found that addition of TPP to host cells comprising the intron variants of the invention suppressed the expression level even further via the action of the thiA riboswitch—in some cases below detection level.

Accordingly, in a first aspect the present invention relates to methods for constructing a recombinant fungal host cell comprising one or more copies of a polynucleotide construct integrated in its genome, said methods comprising:

a) providing a fungal host cell transformed with an integrative polynucleotide construct, said construct comprising a first polynucleotide encoding a selectable marker, wherein the first polynucleotide, a 5' untranslated region thereof and/or a riboswitch operably linked therewith comprises a spliceosomal intron which has 5 nucleotides or less between its branch site and its acceptor site; and a second polynucleotide encoding a polypeptide of interest;
b) cultivating the transformed fungal host cell under conditions conducive for expressing the selectable marker; and
c) isolating a recombinant fungal host cell comprising one or more copies of the polynucleotide construct integrated in its genome.

In a second aspect the invention relates to polynucleotide constructs suitable for transformation into a fungal host cell and integration into the genome of said cell, said construct comprising:

a) a first polynucleotide encoding a selectable marker, wherein the first polynucleotide, a 5' untranslated region thereof and/or a riboswitch operably linked therewith comprises a spliceosomal intron which has 5 nucleotides or less between its branch site and its acceptor site; and
b) a second polynucleotide encoding a polypeptide of interest.

In a third aspect the invention relates to recombinant fungal host cells comprising one or more copies of a polynucleotide construct integrated in its genome, said construct comprising:

a) a first polynucleotide encoding a selectable marker, wherein the first polynucleotide, a 5' untranslated region thereof and/or a riboswitch operably linked therewith comprises a spliceosomal intron which has 5 nucleotides or less between its branch site and its acceptor site; and
b) a second polynucleotide encoding a polypeptide of interest.

In a final aspect, the invention relates to methods of producing a polypeptide of interest, comprising:

a) cultivating a recombinant fungal host cell according to the third aspect; and optionally
b) recovering the polypeptide.

| | | |
|---|---|---|
| ctaacagaTGATAGTCATTG | Intron (6) | SEQ ID NO: 33 |
| ctaactgagatagTTGATTG | Intron (5) | SEQ ID NO: 34 |
| ctaactgaatagTCTGATTG | Intron (4) | SEQ ID NO: 35 |
| ctaactgatagTGATGATTG | Intron (3) | SEQ ID NO: 36 |
| ctaacgatagTTGATGATTG | Intron (2) | SEQ ID NO: 37 |
| ctaacatagTCTGATGATTG | Intron (1) | SEQ ID NO: 38 |
| ctaactagTCATGATGATTG | Intron (0) | SEQ ID NO: 39 |
| ctaacagatgatccTCATTG | Intron (-1) | SEQ ID NO: 40 |

Figure 6:
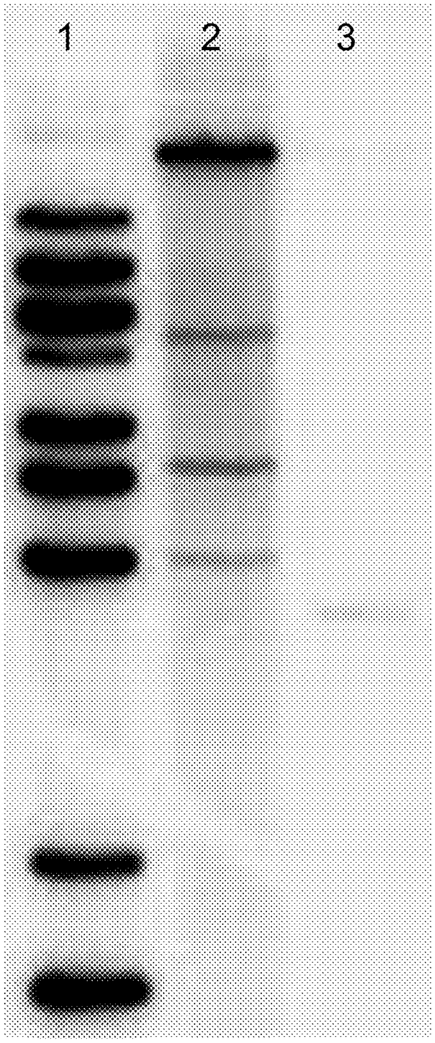

FIG. 6 shows a picture of the Southern blot in example 4 below; Lane 1 is Lambda marker DNA digested with BstEII; Lane 2 is a strain transformed with pCOIs1175 and Lane 3 is the background strain.

DEFINITIONS cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having enzyme activity.

Spliceosomal intron: The term "spliceosomal intron" is another term for nuclear pre-mRNA introns that are characterized by specific intron sequences located at the boundaries between introns and exons. These sequences are recognized by spliceosomal RNA molecules when the splicing reactions are initiated. In addition, they contain a branch site, a particular nucleotide sequence near the 3' end of the intron that becomes covalently linked to the 5' end, the acceptor site, of the intron during the splicing process, generating a branched intron. Apart from these three short conserved elements, nuclear pre-mRNA intron sequences are highly variable.

Intron branch site: In the present context, an intron branch site is defined by the nucleotide sequence "CTRAY", where R=A or G and Y=C or T, in particular as "CTAAC".

Intron acceptor site: An intron acceptor site is often characterized by the two nucleotides AG, but the nucleotide directly upstream may well influence the splicing efficiency, so in the present context, an intron acceptor site is defined as: XAG, wherein X=G or A or T or C.

DETAILED DESCRIPTION OF THE INVENTION

A method for constructing a recombinant fungal host cell comprising one or more copies of a polynucleotide construct integrated in its genome, said method comprising:

a) providing a fungal host cell transformed with an integrative polynucleotide construct, said construct comprising a first polynucleotide encoding a selectable marker, wherein the first polynucleotide, a 5' untranslated region thereof and/or a riboswitch operably linked therewith comprises a spliceosomal intron which has 5 nucleotides or less between its branch site and its acceptor site; and a second polynucleotide encoding a polypeptide of interest;

b) cultivating the transformed fungal host cell under conditions conducive for expressing the selectable marker; and c) isolating a recombinant fungal host cell comprising one or more copies of the polynucleotide construct integrated in its genome; preferably two or more copies; even more preferably three or more copies and most preferably four or more copies.

In a preferred embodiment of the first aspect, the fungal host cell in step (a) has a growth deficiency and the integrative polynucleotide construct complements said growth deficiency when integrated into the genome of the host cell. This allows an optional easy second step between steps (a) and (b) of selecting of a fungal cell, wherein genomic integration of the polynucleotide construct in at least one copy has been successful.

With respect to suitable growth deficiencies, it is preferred that the fungal host cell in step (a) lacks a functional nitrate reductase or nitrite reductase and that the integrative polynucleotide construct comprises a complementing gene encoding a functional nitrate reductase, such as, niaD, or a gene encoding a functional nitrite reductase, such as, niiA, respectively; or that the fungal host cell in step (a) lacks a functional enolase and the integrative polynucleotide construct comprises a complementing gene encoding a functional enolase, such as, acuN.

Other suitable deficiencies relate to required functionalities of a fungal cell grown on a gluconeogenic carbon source. For example, it is preferred that the fungal host of step (a) has an inactive acuK or acuM gene and that the integrative polynucleotide construct comprises a complementing functional acuK or acuM gene, respectively [Hynes M. et al. Transcriptional Control of Gluconeogenesis in *Aspergillus nidulans*, Genetics 176: 139-150 (May 2007)].

Preferably, the integrative polynucleotide construct is randomly integrated in the genome by non-homologous recombination after transformation.

However, often a greater degree of control is preferred, where the integrative polynucleotide construct in step (a) is flanked on one or both side(s) by a homology box of sufficient size and sequence homology to a specific locus in the fungal host cell genome to enable site-specific integration of the integrative polynucleotide construct into said genome by homologous recombination after transformation. Conveniently, the specific locus in the fungal host is the same gene which has been inactivated, for example by partial deletion, to create a growth deficiency. The homology box(es) of the polynucleotide construct can then be either a full copy of the same gene or parts thereof, so that the successful site-specific integration of at least one copy of the polynucleotide construct through homologous recombination between the homology box(es) and the genomic inactivated gene results in the restoration of a functional gene in the genome or a replacement with a functional version of the same gene.

Preferably, the spliceosomal intron has 4 nucleotides or less between its branch site and its acceptor site; preferably 3 nucleotides or less; more preferably 2 nucleotides or less; even more preferably 1 nucleotide; still more preferably the spliceosomal intron has 0 nucleotides between its branch site and its acceptor site and most preferably the branch site and the acceptor site of spliceosomal intron overlap by at least one nucleotide. Alternatively, it is preferred that the spliceosomal intron comprises a nucleotide sequence selected from the group of intron nucleotide sequences consisting of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39 and SEQ ID NO: 40.

We have already mentioned, that the inventors carried out the method of the first aspect using a spliceosomal intron of the thiA riboswitch from *A. oryzae* and showed that this enabled an even greater degree of expression level control of the downstream gene(s). Accordingly, in a preferred embodiment of the method of the first aspect, the first polynucleotide of the integrative polynucleotide construct has a riboswitch operably linked therewith; preferably the riboswitch is derived from the thiA or nmtA genes in *Aspergillus oryzae.*

Preferably, the first polynucleotide of the integrative polynucleotide construct encodes the selectable marker orotidine-5' phosphate decarboxylase or PyrG.

In a preferred embodiment of the invention, the polypeptide of interest encoded by the second polynucleotide of the integrative polynucleotide construct comprises an enzyme; preferably a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

Nucleic Acid Constructs

A second aspect of the invention relates to a polynucleotide construct suitable for transformation into a fungal host cell and integration into the genome of said cell, said construct comprising: a first polynucleotide encoding a selectable marker, wherein the first polynucleotide, a 5' untranslated region thereof and/or a riboswitch operably linked therewith comprises a spliceosomal intron which has 5 nucleotides or less between its branch site and its acceptor site; and a second polynucleotide encoding a polypeptide of interest.

In a preferred embodiment of the second aspect, the polynucleotide construct comprises a gene encoding a functional nitrate reductase, such as, niaD, a gene encoding a functional nitrite reductase, such as, niiA, or a gene encoding a functional enolase, such as, acuN.

In a preferred embodiment of the second aspect, the polynucleotide construct is flanked on one or both side(s) by a homology box of sufficient size and sequence homology to a specific locus in the fungal host cell genome to enable site-specific integration of the integrative polynucleotide construct into said genome by homologous recombination after transformation.

Preferably, the spliceosomal intron has 4 nucleotides or less between its branch site and its acceptor site; preferably 3 nucleotides or less; more preferably 2 nucleotides or less; even more preferably 1 nucleotide; still more preferably the spliceosomal intron has 0 nucleotides between its branch site and its acceptor site and most preferably the branch site and the acceptor site of spliceosomal intron overlap by at least one nucleotide. Or alternatively, the spliceosomal intron comprises a nucleotide sequence selected from the group of intron nucleotide sequences consisting of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39 and SEQ ID NO: 40.

In a preferred embodiment the first polynucleotide, located in the integrative polynucleotide construct of the invention, has a riboswitch operably linked therewith; preferably the riboswitch is derived from the thiA or nmtA genes in *Aspergillus oryzae.*

Preferably, the first polynucleotide of the integrative polynucleotide construct encodes the selectable marker orotidine-5' phosphate decarboxylase or PyrG.

It is preferable, that the polypeptide of interest encoded by the second polynucleotide of the integrative polynucleotide construct comprises an enzyme; preferably a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The present invention also relates to nucleic acid constructs comprising a first and/or second polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995*, Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus olyzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

A third aspect of the invention relates to a recombinant fungal host cell comprising one or more copies of a polynucleotide construct integrated in its genome, said construct comprising: a first polynucleotide encoding a selectable marker, wherein the first polynucleotide, a 5' untranslated region thereof and/or a riboswitch operably linked therewith comprises a spliceosomal intron which has 5 nucleotides or less between its branch site and its acceptor site; and a second polynucleotide encoding a polypeptide of interest.

In a preferred embodiment of the third aspect, the fungal host cell comprises two or more copies of the polynucleotide construct integrated in its genome; even more preferably three or more copies and most preferably four or more copies of the polynucleotide construct integrated in its genome.

It is preferable that the integrative polynucleotide construct has been randomly integrated into the genome by non-homologous recombination or that it has been site-specifically integrated into the genome by homologous recombination; preferably into a gene encoding a nitrate reductase or nitrite reductase; more preferably into a gene required for gluconeogenesis; and most preferably into the niaD, niiA, acuN, acuK or acuM locus.

In a preferred embodiment the spliceosomal intron has 4 nucleotides or less between its branch site and its acceptor site; preferably 3 nucleotides or less; more preferably 2 nucleotides or less; even more preferably 1 nucleotide; still more preferably the spliceosomal intron has 0 nucleotides between its branch site and its acceptor site and most preferably the branch site and the acceptor site of spliceosomal intron overlap by at least one nucleotide.

In another preferred embodiment of the third aspect, the spliceosomal intron comprises a nucleotide sequence selected from the group of intron nucleotide sequences consisting of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39 and SEQ ID NO: 40.

It is preferred that the first polynucleotide of the integrative polynucleotide construct has a riboswitch operably linked therewith; preferably the riboswitch is derived from the thiA or nmtA genes in *Aspergillus oryzae*; even more preferably the riboswitch comprises the riboswitch of the thiA or nmtA genes in *Aspergillus oryzae*; most preferably the riboswitch consists of the riboswitch of the thiA or nmtA genes in *Aspergillus oryzae.*

Also preferred is that the first polynucleotide of the integrative polynucleotide construct encodes the selectable marker orotidine-5' phosphate decarboxylase or PyrG.

Another preferred embodiment of the third aspect is that the polypeptide of interest encoded by the second polynucleotide of the integrative polynucleotide construct comprises an enzyme; preferably a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

Preferably, the second polynucleotide of polynucleotide construct of the present invention is operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a fungal cell.

"Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium mops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chtysosporium, Phlebia radiata, Pleurotus etyngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of interest, comprising cultivating a recombinant fungal host cell according to the third aspect, and optionally recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

EXAMPLES

Materials and Methods

Growth of Strains on Solid Agar and in Liquid Medium

All strains have been grown on plates at 30° C. after transformation. When using liquid media, incubation was done at 30° C. with shaking at 180 rpm.

Lipase Assay

Dilution buffer:
50 mM Tris pH 7.5
10 mM CaCl2
0.1% Triton x-100
Substrate stock solution: 117 μl p-Nitrophenyl valerate (sigma N4377) is diluted in 10 ml Methanol
Substrate: 10 ml dilution buffer is added 100 μl substrate stock solution.

10 μl sample is added 1 ml substrate and product formation is followed by measuring the absorbance at 405 nm.

Sucrose Medium
1M Sucrose
0.18 μM $Na_2B_4O_7$
2.3 μM $CuSO_4$
4.7 μM $FeSO_4$
4.7 μM $MnSO_4$
3.6 μM $Na_2MoO_4$
45 μM $ZnSO_4$
7 mM KCl
4.3 mM $MgSO_4$
11.2 mM $KH_2PO_4$ In-Fusion Cloning In-Fusion Cloning was done using the In-Fusion cloning kit and manuals supplied by Clontech Laboratories, Inc.

Example 1: Making an Intron Library

The thiA promoter from *Aspergillus oryzae* and its 5' untranslated region (UTR) riboswitch were amplified using the primers:

```
P722 (SEQ ID NO: 1):
atctcgagctcgcgaaagcttttcggtaaatacactatcacacac;
and

P723 (SEQ ID NO: 2):
gagctcctcatggtggatccactagtgcatgccaagttgcaatgactat
catctg.
```

Figure 1:
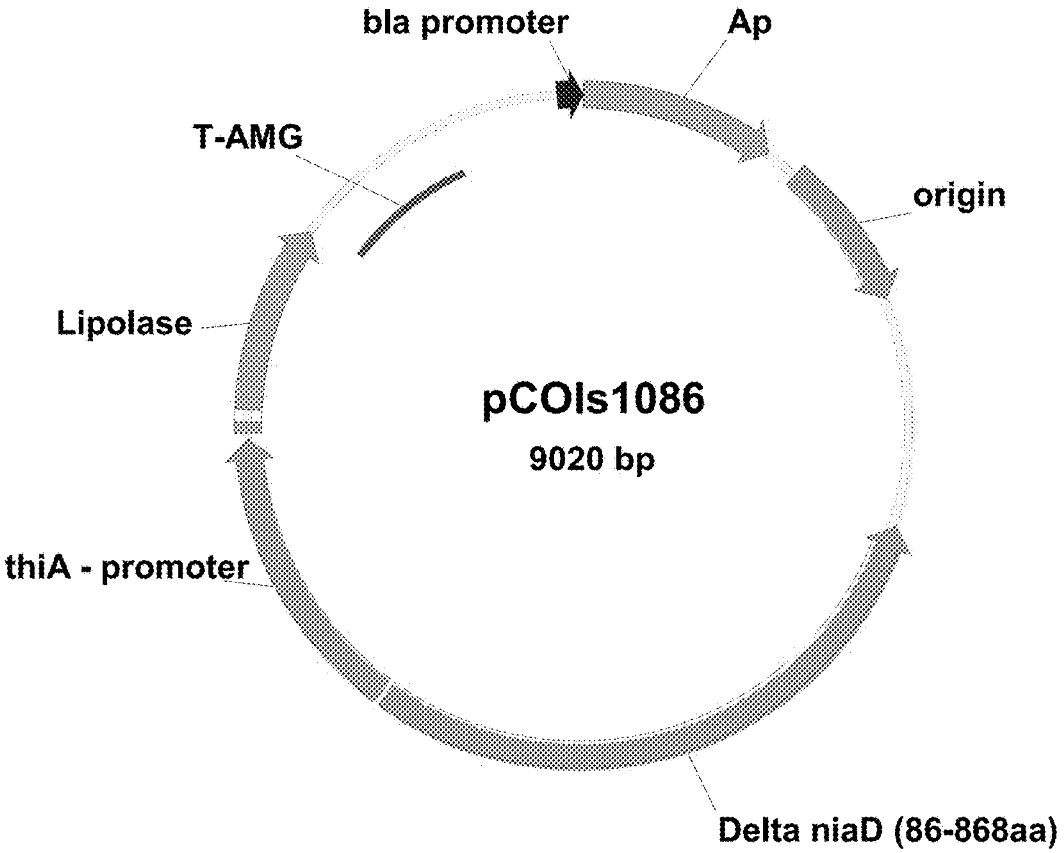
FIG. 1 shows a schematic overview of plasmid pCOIs1086 of the examples below.

The resulting 1338 bp fragment was In-Fusion cloned, using the Clontech In-Fusion kit, to the 7718 bp HindIII/BamHI fragment from the vector pCOIs207 (SEQ ID NO:21). The resulting vector was named pCOIs1086 and is shown in FIG. 1.

Plasmid pJaL1262 (full sequence shown in SEQ ID NO:22) was cut with SphI/AfeI, and the resulting 4840 bp fragment was purified.

Plasmid pCOIs1086 was cut with NheI, blunt-ended with Klenow and cut again with SphI and KasI. The resulting 4677 bp fragment was purified and ligated to the 4840 bp fragment from pJaL1262 and the resulting vector was named pCOIs1123.

The pyrG gene from *Aspergillus oryzae* was amplified from chromosomal DNA from *Aspergillus oryzae* A1560 using the primers:

```
P766 (SEQ ID NO: 3):
gtcattgcaacttggccaacatgtcttccaagtcgc;
and

P767 (SEQ ID NO: 4):
accatgattacgccgcattagtgataccccactctaag.
```

Figure 2:
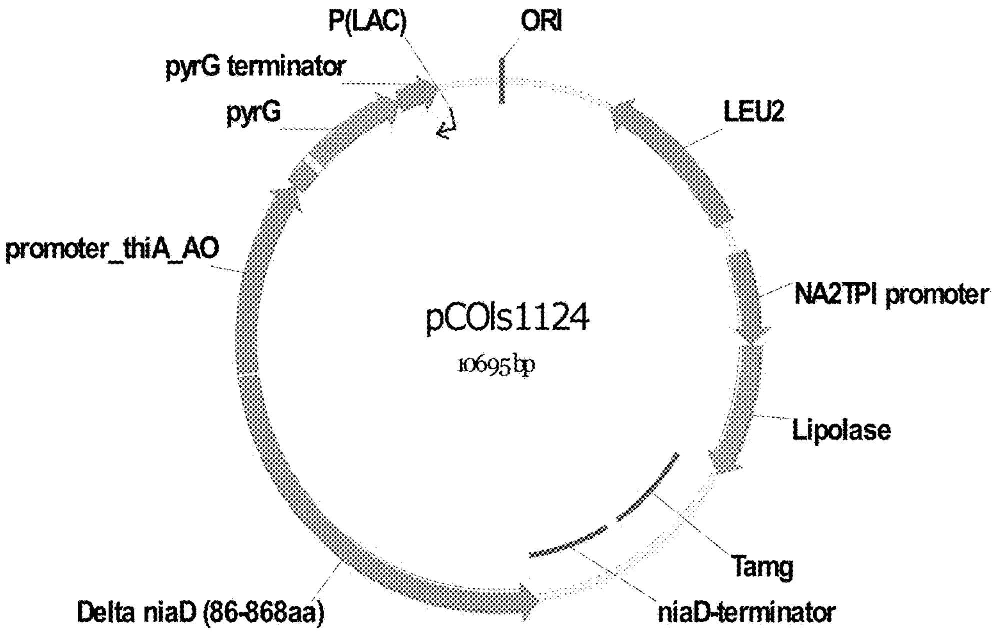
FIG. 2 shows a schematic overview of plasmid pCOIs1124 of the examples below.

The PCR product was In-Fusion cloned to the vector pCOIs1123 that had been linearized with SphI. The resulting vector was named pCOIs1124 and is shown schematically in FIG. 2.

An SOE-PCR product was made using pCOIs1124 as the template and the primers:

```
P722 (SEQ ID NO: 1):
atctcgagctcgcgaaagcttttcggtaaatacactatcacacac

P769 (SEQ ID NO: 5):
ccgcggcaagttgcaatgactatcatctg

P771 (SEQ ID NO: 6):
aattcgaaggcctcccatcaccatcaccatcactaag

P503 (SEQ ID NO: 7):
acatgatcatataaccaattgccctcatccccatcctttaac
```

Figure 3:
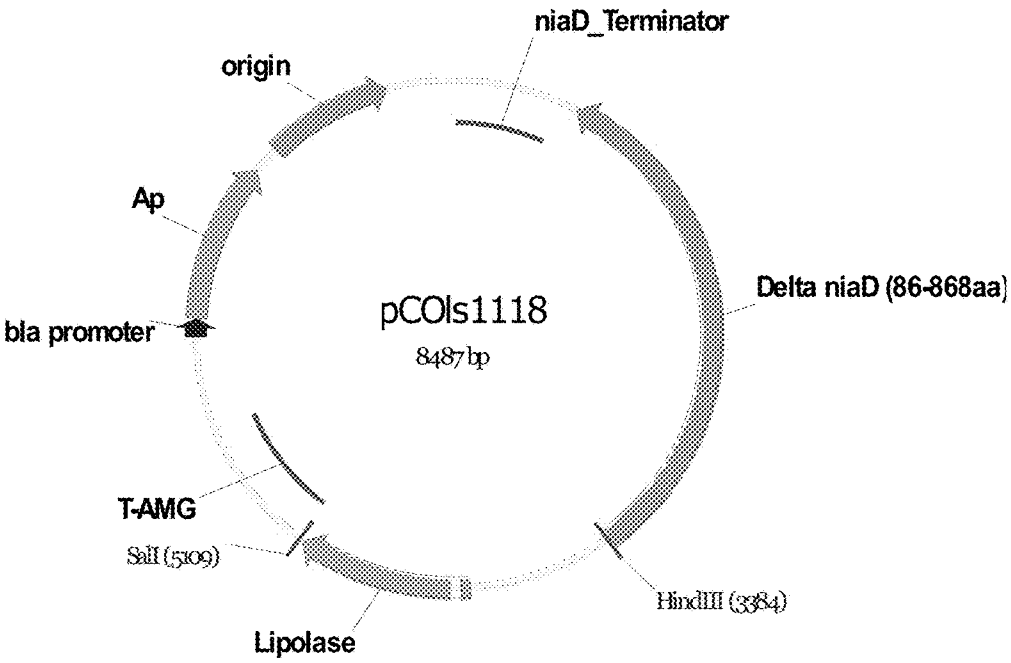
FIG. 3 shows a schematic overview of plasmid pCOIs1118 of the examples below.
Figure 4:
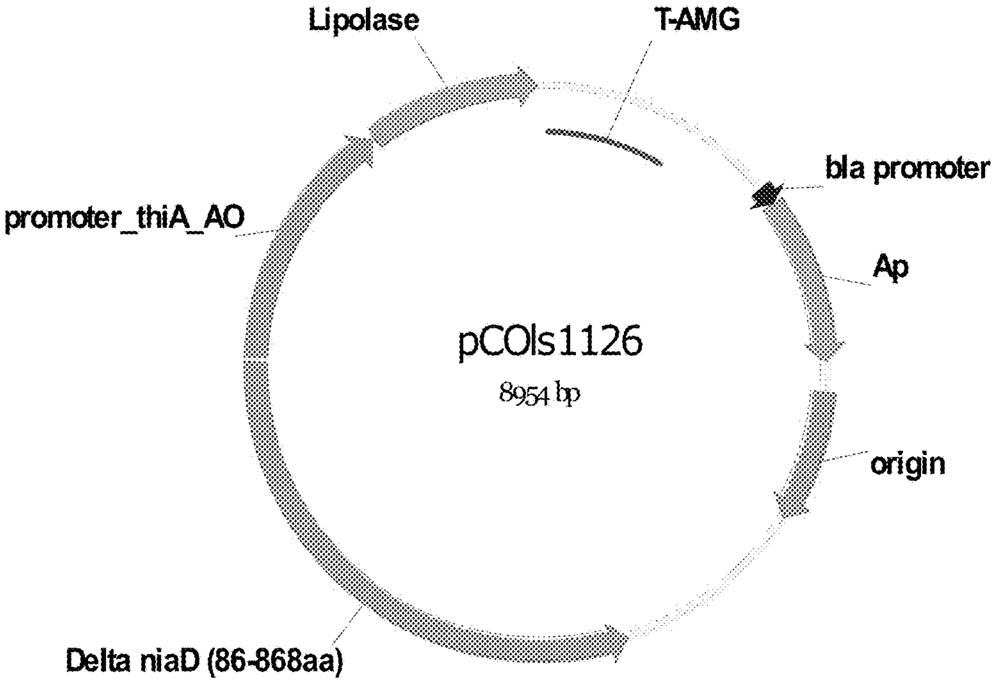
FIG. 4 shows a schematic overview of plasmid pCOIs1126 of the examples below.

Plasmid pCOIs1118 shown in FIG. 3 (full sequence in SEQ ID NO:23) was cut with HindIII and SalI. The resulting 6762 bp fragment was ligated to the SOE-PCR product that had been cut with HindIII and SalI. The resulting plasmid was named pCOIs1126 and is shown in FIG. 4.

Eight different constructs were made that had different distances between the intron branch site "ctaac" (FIG. 5, shaded) and the intron acceptor site "tag" (FIG. 5, underscore) of the thiA riboswitch. The number of bases between the two sites were varied between 0-6 bp and one construct had the acceptor site overlapping with and forming a part of the branch site, resulting in the sequence "ctaacag", where the branch site is "ctaac" and the acceptor site "cag". The latter variant was named "Intron(−1)". The others were named "Intron(0)", "Intron(1)", "Intron(2), "Intron(3)", "Intron(4)", "Intron(5)" and finally "Intron(6)" which is the wild type sequence (FIG. 5).

Figure 5:
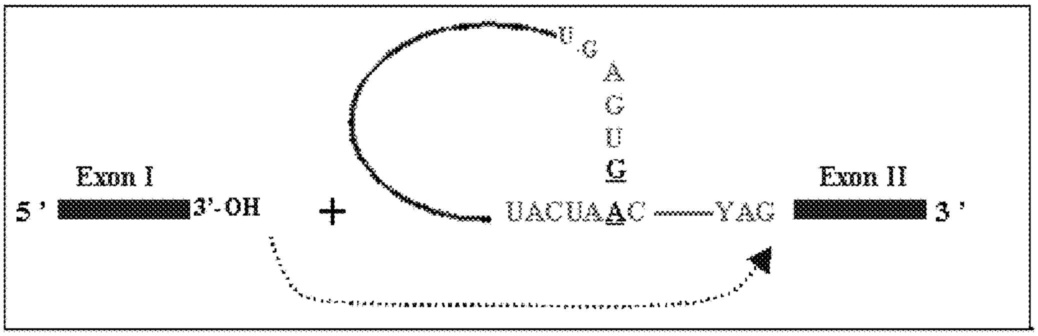
FIG. 5 shows a general illustration of spliceosomal intron RNA processing as well as eight different construct made with different distances between the intron branch site "ctaac" (shaded) and the intron acceptor site "tag" (shaded) in the thiA riboswitch intron. The number of bases between the two sites were varied between 0-6 bp and one construct had the acceptor site overlapping with and forming a part of the branch site, resulting in the sequence "ctaacag", where the branch site is "ctaac" and the acceptor site "cag". The latter variant was named "Intron(−1)". The others were named "Intron(0)", "Intron(1)", "Intron(2), "Intron(3)", "Intron(4)", "Intron(5)" and finally "Intron(6)" which is the wild type sequence (FIG. 5), as shown in the table below.

There are two stop-codons "TGATAG" in the same reading frame in the wildtype sequence Intron(6) (FIG. 5). It was decided to maintain at least two stop-codons in the variant constructs in the same reading frame as in the wildtype sequence in order to avoid any readthrough from unknown upstream gene(s). This was achieved by modifying the sequences slightly besides just removing one nucleotide from between the branch site and the acceptor site. So the sequences are not completely identical but this was not expected to have any significant effect on the splicing efficiencies of the constructs compared to the shortening of the distance between the branch and acceptor sites.

The constructs were made by PCR of the riboswitch in plasmid pCOIs1124 using the forward-primer: P782 (SEQ ID NO:8): ccttgatactctgtgagcgct; and the following reverse primers, one per construct:

```
P783 (SEQ ID NO: 9):
gagctcctcatggggccgcggcaatgactatcatctgttagccattccat
caacagg

P784 (SEQ ID NO: 10):
gagctcctcatggggccgcggcaatcaactatctcagttagccattccat
caacagg

P785 (SEQ ID NO: 11):
gagctcctcatggggccgcggcaatcagactattcagttagccattccat
caacagg

P786 (SEQ ID NO: 12):
gagctcctcatggggccgcggcaatcatcactatcagttagccattccat
caacagg

P787 (SEQ ID NO: 13):
gagctcctcatggggccgcggcaatcatcaactatcgttagccattccat
caacagg

P788 (SEQ ID NO: 14):
gagctcctcatggggccgcggcaatcatcagactatgttagccattccat
caacagg

P789 (SEQ ID NO: 15):
gagctcctcatggggccgcggcaatcatcatgactagttagccattccat
caacagg

P792 (SEQ ID NO: 16):
gagctcctcatggggccgcggcaatgaggatcatctgttagccattccat
caacagg
```

The PCR constructs were each In-Fusion cloned to the 7661 bp HindIII/SacII fragment from plasmid pCOIs1126. Table 1 below gives an overview of the primers used for creating the alternative introns (shown in FIG. 5) and the names of the resulting plasmids.

TABLE 1

| Intron variant | Reverse-primer | Resulting plasmid |
|---|---|---|
| Intron(6) | SEQ ID NO: 9 | pCOIs1135 |
| Intron(5) | SEQ ID NO: 10 | pCOIs1136 |
| Intron(4) | SEQ ID NO: 11 | pCOIs1137 |
| Intron(3) | SEQ ID NO: 12 | pCOIs1138 |
| Intron(2) | SEQ ID NO: 13 | pCOIs1139 |
| Intron(1) | SEQ ID NO: 14 | pCOIs1140 |

TABLE 1-continued

| Intron variant | Reverse-primer | Resulting plasmid |
|---|---|---|
| Intron(0) | SEQ ID NO: 15 | pCOIs1141 |
| Intron(−1) | SEQ ID NO: 16 | pCOIs1148 |

Example 2: Use of Intron Variants to Regulate Marker Expression

All the riboswitch intron variants were fused to the lipase reporter gene of pCOIs1126. The resulting constructs were integrated at the niaD locus in one copy in an *Aspergillus oryzae* strain having a partially deleted niaD gene which was repaired by the individual in-coming constructs, thereby enabling growth on nitrate as the sole nitrogen source.

Transformants were grown in Sucrose Medium for three days and lipase activity was measured on the supernatant as detailed above. The lipase activities found are summarized in table 2 below:

TABLE 2

| Intron variant | Relative reporter activity | % of wild type |
|---|---|---|
| Intron(6) | 0.244 | 100 |
| Intron(5) | 0.231 | 95 |
| Intron(4) | 0.178 | 73 |
| Intron(3) | 0.066 | 27 |
| Intron(2) | 0.018 | 7 |
| Intron(1) | 0.010 | 4 |
| Intron(0) | 0.006 | 2.5 |
| Intron(−1) | 0.000 | 0 |

From these results, we conclude that it is possible to make a series of intron-containing 5-UTRs with different intron splicing efficiencies providing a range of expression levels of the downstream operably linked gene. When the splicing efficiency is lowered, a proportion of the expressed mRNAs will contain the intron sequence, resulting in translation initiation and immediate translation termination within the intron, preventing translation of the downstream gene product—as demonstrated with the lipase activity in table 2.

Example 3: Intron Riboswitch Variants are Repressible by Thiamine

Four of the thiA riboswitch intron variant strains: (6), (3), (0) and (−1), were grown in sucrose medium for 48 hours without or with a supplement of thiamine (10 uM of ThiamineHCl), respectively. Samples were analysed for lipase activity as already shown—the results are in table 3 below.

We were unable to determine ("UD") any activity from Intron(0) and Intron(−1), but the wildtype sequence in Intron(6) was actually repressed by almost a factor of 100 with addition of thiamine, as expected, and Intron(3) was repressed by almost a factor of 10 on top of the reduction due to the shortened branch and acceptor site distance in that variant.

TABLE 3

| Intron variant | −ThiamineHCl | +ThiamineHCl |
|---|---|---|
| Intron(6) | 100 | 1.6 |
| Intron(3) | 8.3 | 1.4 |
| Intron(0) | UD | UD |
| Intron(−1) | UD | UD |

Example 4: Use of Intron Variants to Select for Transformed Strains with a High Copy Number of an Integrated Gene This example illustrates the use of the intron variants and their thiamine repression to control expression of a selectable marker (rather than an expression reporter) in order to obtain transformants with a high gene copy number of the marker gene. The marker gene is linked with an expression cassette comprising a gene of interest which we would like to express at a high level; the expression cassette will be duplicated along with the marker gene, thus increase its copy number as well.

The wild type thiA riboswitch, Intron(6), and three intron variants, Intron(3), Intron(0) and Intron(−1) were cloned in front of the pyrG gene from *Aspergillus oryzae*. The constructs were fused to a lipase expression cassette. Expression from the cassette would be used as a benchmark for the gene copy number.

A plasmid pCOIs1130 was made by doing SOE-PCR on pCOIs1124 (FIG. 2) using the primerpairs P722/P769 and P775/767:

```
P722 (SEQ ID NO: 1):
atctcgagctcgcgaaagcttttcggtaaatacactatcacacac

P769 (SEQ ID NO: 5):
ccgcggcaagttgcaatgactatcatctg

P775 (SEQ ID NO: 17):
gatagtcattgcaacttgccgcggcaccatgtcttccaagtcgcaattgac

P767 (SEQ ID NO: 18):
accatgattacgccgcattagtgataccccactctaag
```

An SOE-PCR was then made using the primerpair P722/P767 and the resulting fragment was cut with HindIII/BsiWI and ligated to a 8389 bp HindIII/BsiWI fragment from pCOIs1124. The resulting plasmid was named pCOIs1130.

Construction of Four Intron Variant Constructs Fused to pyrG

The plasmid pCOIs1130 was cut with HindIII/SacII and the 9406 bp fragment was purified.

The plasmids pCOIs1135, pCOIs1138, pCOIs1141 and pCOIs1148 (see table 1) were all cut with HindIII/SacII and the 1286 bp fragment was ligated to the 9406 bp fragment from pCOIs1130. The resulting plasmids were named according to table 4 below.

TABLE 4

| Intron variant | Plasmid |
|---|---|
| Intron(6) | pCOIs1172 |
| Intron(3) | pCOIs1173 |
| Intron(0) | pCOIs1174 |
| Intron(−1) | pCOIs1175 |

The four plasmids pCOIs1172, pCOIs1173, pCOIs1174 and pCOIs1175 were all individually transformed in an *A. oryzae* strain that had the pyrG deleted and had a partial niaD gene that could be repaired by integrating the plasmid at the niaD locus. The transformation mixtures were spread on plates containing three different media:

A) Sucrose Medium+10 mM $NaNO_3$+20 mM Uridine

B) Sucrose Medium+10 mM $NaNO_3$

C) Sucrose Medium+10 mM $NaNO_3$+10 μM Thiamine-HCl

Transformants were counted on the different plates and the results are shown in table 5 below.

TABLE 5

| Intron variant | Medium A | Medium B | Medium C |
|---|---|---|---|
| Intron(6) | 100 | 100 | 100 |
| Intron(3) | 100 | 79 | 63 |
| Intron(0) | 100 | 33 total<br>6 large | 22 total<br>4 large |
| Intron(−1) | 100 | 24 total<br>6 large | 23 total<br>7 large |

On medium B and medium C, where expression of the pyrG is required, we found transformants that grew differently. We categorized some of the transformants as being large which were those transformants that were healthy and grew with the same speed as a wild type strain. The other transformants grew much more slowly.

The number of transformants on Medium C is lower than on Medium B for Intron(3) and Intron(0), indicating that there is a thiamine effect which represses expression of the pyrG gene. We conclude that when using Intron(3), Intron(0) and Intron(−1) in front of the pyrG marker, more than one copy of the pyrG gene is needed in order for the cell to grow.

We saw that the so-called large colonies obtained with the Intron(0) and Intron(−1) constructs contain a very high copy-number of the expression construct. This was determined by Southern analysis digesting chromosomal DNA with AatII and AfeI and then using part of the niaD integration fragment as the probe (see FIG. 6). In FIG. 6, one can see that the background strain has one fragment binding the probe, whereas the strain transformed with pCOIs1175 show binding of the probe to fragments containing sequences flanking the insertion site as well as the whole expression construct, which show a band with a very high intensity; indicating many copies of the expression construct.

Example 5: Riboswitches in Tandem Provides a Broader Range of Thiamine Repression Multiple thiA riboswitches in front of a specific gene will increase the likelihood that the messenger-RNA will enter the cytoplasm with one of the riboswitches intact, if the thiamine concentration within the cell allows for some degree of occupation of the TPP binding site. Thus, at a high concentration of thiamine, two or more thiA riboswitches should facilitate increased thiamine repression of an operably linked downstream coding sequence.

A thiA riboswitch was constructed synthetically in one or two copies and placed after the thiA riboswitch and in front of the lipase reporter gene of pCOIs1126 (FIG. 4), resulting in the plasmids pCOIs1142 (2 riboswitches) and pCOIs1143 (3 riboswitches).

The 5'-end of the riboswitches was SEQ ID NO:19: ccgctcccacacaattctct

The 3'-end of the riboswitches was SEQ ID NO:20: tcattgcaacttg

The constructs were integrated in *A. oryzae* at the niaD locus in one copy resulting in the strains shown in table 7.

TABLE 7

| Strain | Plasmid | Riboswitch copies | Reporter activity |
|---|---|---|---|
| Ribo1 | pCOIs1126 | 1 | 100% |
| Ribo2 | pCOIs1142 | 2 | 48% |
| Ribo3 | pCOIs1143 | 3 | 32% |

The three strains in Table 7 were grown in sucrose medium without added thiamine for 48 hours at 30° C. Samples were taken and analysed for lipase reporter activity, as mentioned above.

The activity from the Ribo2 strain in table 7 was only 48% compared to the Ribo1 strain and the Ribo3 strain only produced 32% of the activity found in the Ribo1 strain. These results demonstrate that the presence of two or more thiA riboswitches in front of a given gene will lower its expression accordingly.

We also performed a similar experiment with addition of 1 uM of thiamine to the medium, but the expression level from the Ribo2 and Ribo3 strains were below the detection level of our lipase assay. This indicates a high degree of repression using these tandem constructs as well as a broader range of repression than when using only one riboswitch.

Example 6: Riboswitch Introns Inside an Open Reading Frame Overcomes any Problem with Ribosome Reinitiation We have observed that with any riboswitch construct we put in front of the pyrG marker and with a concentration of thiamine that we expected to give full repression, we could still always obtain a few transformants. We believe this is either due to ribosome read-through of the riboswitch intron without initiating at any of the ATG codons present in the intron or from reinitiation events at the pyrG start codon.

To bring expression of the pyrG marker to even lower levels, the riboswitch intron can be moved inside the pyrG open reading frame. This will prevent formation of a functional pyrG expression product if the intron has not been spliced out.

Example 7: Making a Synthetic Intron Library

A synthetic intron was constructed from consensus sequences of the donor site, branch site and acceptor site of the second intron in the riboswitch from the thiA gene from *Aspergillus oryzae*. The synthetic intron contains two very efficient translation start sites both having a very good kozak sequence and being in different frames. These two open reading frames within the intron are terminated before the intron branch site. Moreover, the intron contains six other translation start sites with less efficient kozaks, thus contributing less to translational initiation of ribosomes having missed upstream translation start sites. The modified intron was fused to the sequence “tgtacattgattaattgacaccATG” (SEQ ID NO:24), which contains stop codons in all three reading frames, which will block ribosomes translating from translation start sites within the intron. Moreover SEQ ID NO:24 contains at the 3'-end the kozak and translation initiation codon for the lipase reporter gene used in the example.

Eight different variants of the synthetic intron were made by changing the distance between the branch site “ctaac” sequence and the splice acceptor site “tag”. In the eighth sequence, Intron(−1), the splice acceptor site had the first base of the triplet “tag” deleted so the branch site and acceptor site were fused into the sequence “ctaacag”, where the acceptor site is part of the branch site. See Table 8 for an overview of the eight intron variants.

All eight intron variants were cloned in the reporter construct present in pCOIs1126 between the splice branch site and the translational start codon of the lipase reporter gene. The resulting constructs were integrated individually at the niaD locus in one copy in an *Aspergillus oryzae* strain having a partially deleted niaD gene, which was repaired by the individual in-coming construct, thereby enabling growth on nitrate as the sole nitrogen source. The individual construct was verified to be present in only one copy in order to exclude a copy number effect on the results.

TABLE 8

| Splice site variant | Strain | SEQ ID NO |
|---|---|---|
| ctaacagttgatagtgtacat*tgattaattga*caccATG | Intron(6) | SEQ ID NO: 25 |
| ctaacgttgatagtgtacat*tgattaattga*caccATG | Intron(5) | SEQ ID NO: 26 |
| ctaacttgatagtgtacat*tgattaattga*caccATG | Intron(4) | SEQ ID NO: 27 |
| ctaactgatagtgtacat*tgattaattga*caccATG | Intron(3) | SEQ ID NO: 28 |
| ctaacgatagtgtacat*tgattaattga*caccATG | Intron(2) | SEQ ID NO: 29 |
| ctaacatagtgtacat*tgattaattga*caccATG | Intron(1) | SEQ ID NO: 30 |
| ctaactagtgtacat*tgattaattga*caccATG | Intron(0) | SEQ ID NO: 31 |
| ctaacagtgtacat*tgattaattga*caccATG | Intron(-1) | SEQ ID NO: 32 |

Because of the requirement of some spacing between the branch site and the splice acceptor site for efficient splicing, the constructs with the less spacing had less expression of the reporter gene, because translation will be initiated at the translation start sites within the non-spliced intron and terminated before reaching the lipase reporter gene. Varying spacing between the branch site and the acceptor is thereby an efficient way of varying gene expression. In this example, where the thiA promoter and thiA riboswitch have been used, additional variation can even be obtained by varying the exogenous supply of thiamine. However, the endogenous thiamine concentration will vary in different growth phases influencing thiamine repression, whereas the efficiency of splicing is expected to be constant. Thus, a constant regulation of gene expression can be obtained by using splice site variants instead of using inducible or repressible promoters. This can be important when a constant and exact level of gene expression is wanted.

The invention claimed is:

1. A polynucleotide construct suitable for transformation into a fungal host cell and integration into the genome of said cell, said construct comprising:

(a) a first polynucleotide encoding a selectable marker, wherein the first polynucleotide, a 5' untranslated region thereof and/or a riboswitch operably linked therewith comprises a spliceosomal intron which has 5 or less nucleotides between its branch site and its acceptor site; and (b) a second polynucleotide encoding a polypeptide of interest.

2. The polynucleotide construct of claim 1, wherein the fungal host cell is a filamentous fungal host cell.

3. The polynucleotide construct of claim 1, wherein the fungal host cell is a yeast host cell.

4. The polynucleotide construct of claim 1, which further comprises a gene encoding a functional nitrate reductase, a gene encoding a functional nitrite reductase, or a gene encoding a functional enolase.

5. The polynucleotide construct of claim 1, which is flanked on one or both side(s) by a homology box of sufficient size and sequence homology to a specific locus in the fungal host cell genome to enable site-specific integration of the integrative polynucleotide construct into said genome by homologous recombination after transformation.

6. The polynucleotide construct of claim 1, wherein the spliceosomal intron has 4 nucleotides or less between its branch site and its acceptor site.

7. The polynucleotide construct of claim 1, wherein the spliceosomal intron comprises a nucleotide sequence selected from the group of intron nucleotide sequences consisting of SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 38, SEQ ID NO: 39 and SEQ ID NO: 40.

8. The polynucleotide construct of claim 1, wherein the first polynucleotide has a riboswitch operably linked therewith.

9. The polynucleotide construct of claim 1, wherein the first polynucleotide of the integrative polynucleotide construct encodes the selectable marker orotidine-5'-phosphate decarboxylase or PyrG.

10. The polynucleotide construct of claim 1, wherein the polypeptide of interest encoded by the second polynucleotide of the integrative polynucleotide construct comprises an enzyme.

11. A recombinant fungal host cell comprising one or more copies of the polynucleotide construct of claim 1 integrated in its genome.

12. The recombinant fungal host cell of claim 11 which comprises two or more copies of the polynucleotide construct integrated in its genome.

13. The recombinant fungal host cell of claim 11 which is a filamentous fungal host cell.

14. The recombinant fungal host cell of claim 11 which is a yeast host cell.

15. The recombinant fungal host cell of claim 11, wherein the integrative polynucleotide construct is randomly integrated into the genome by non-homologous recombination.

16. The recombinant fungal host cell of claim 11, wherein the integrative polynucleotide construct is site-specifically integrated into the genome by homologous recombination.

17. The recombinant fungal host cell of claim 11, wherein the spliceosomal intron has 4 nucleotides or less between its branch site and its acceptor site.

18. The recombinant fungal host cell of claim 11, wherein the spliceosomal intron comprises a nucleotide sequence selected from the group of intron nucleotide sequences consisting of SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 38, SEQ ID NO: 39 and SEQ ID NO: 40.

19. The recombinant fungal host cell of claim 11, wherein the first polynucleotide of the integrative polynucleotide construct has a riboswitch operably linked therewith.

20. The recombinant fungal host cell of claim 11, wherein the first polynucleotide of the integrative polynucleotide construct encodes the selectable marker orotidine-5'-phosphate decarboxylase or PyrG.

21. The recombinant fungal host cell of claim 11, wherein the polypeptide of interest encoded by the second polynucleotide of the integrative polynucleotide construct comprises an enzyme.

22. A method of producing a polypeptide of interest, comprising:

(a) cultivating the recombinant fungal host cell of claim 11; and optionally (b) recovering the polypeptide.

23. The polynucleotide construct of claim 2, wherein the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

24. The polynucleotide construct of claim 3, wherein the yeast host cell is a *Candida, Hansenula, Kluyveromyces, Pichia, Saccharomyces, Schizosaccharomyces*, or *Yarrowia* cell.

25. The polynucleotide construct of claim 4, wherein the gene encoding a functional nitrate reductase is niaD.

26. The polynucleotide construct of claim 4, wherein the gene encoding a functional nitrite reductase is niiA.

27. The polynucleotide construct of claim 4, wherein the gene encoding a functional enolase is acuN.

28. The polynucleotide construct of claim 6, wherein the spliceosomal intron has 3 nucleotides or less between its branch site and its acceptor site.

29. The polynucleotide construct of claim 6, wherein the spliceosomal intron has 2 nucleotides or less between its branch site and its acceptor site.

30. The polynucleotide construct of claim 6, wherein the spliceosomal intron has 1 nucleotide between its branch site and its acceptor site.

31. The polynucleotide construct of claim 6, wherein the branch site and the acceptor site of the spliceosomal intron overlap by at least one nucleotide.

32. The polynucleotide construct of claim 8, wherein the riboswitch is derived from the thiA gene in *Aspergillus oryzae*.

33. The polynucleotide construct of claim 8, wherein the riboswitch is derived from the nmtA gene in *Aspergillus oryzae*.

34. The recombinant fungal host cell of claim 11 which comprises three or more copies of the polynucleotide construct integrated in its genome.

35. The recombinant fungal host cell of claim 11 which comprises four or more copies of the polynucleotide construct integrated in its genome.

36. The recombinant fungal host cell of claim 13, wherein the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

37. The recombinant fungal host cell of claim 14, wherein the yeast host cell is a *Candida, Hansenula, Kluyveromyces, Pichia, Saccharomyces, Schizosaccharomyces*, or *Yarrowia* cell.

38. The recombinant fungal host cell of claim 16, wherein the integrative polynucleotide construct is site-specifically integrated into the genome by homologous recombination into a gene encoding a nitrate reductase, a gene encoding a nitrite reductase, or a gene encoding an enolase.

39. The recombinant fungal host cell of claim 38, wherein the nitrate reductase gene is niiD.

40. The recombinant fungal host cell of claim 38, wherein the nitrite reductase gene is niiA.

41. The recombinant fungal host cell of claim 38, wherein the enolase gene is acuN, acuK, or acuM.

42. The recombinant fungal host cell of claim 17, wherein the spliceosomal intron has 3 nucleotides or less between its branch site and its acceptor site.

43. The recombinant fungal host cell of claim 17, wherein the spliceosomal intron has 2 nucleotides or less between its branch site and its acceptor site.

44. The recombinant fungal host cell of claim 17, wherein the spliceosomal intron has 1 nucleotide between its branch site and its acceptor site.

45. The recombinant fungal host cell of claim 17, wherein the branch site and the acceptor site of the spliceosomal intron overlap by at least one nucleotide.

46. The recombinant fungal host cell of claim 19, wherein the riboswitch is derived from the thiA gene in *Aspergillus oryzae*.

47. The recombinant fungal host cell of claim 19, wherein the riboswitch is derived from the nmtA gene in *Aspergillus oryzae*.

* * * * *